US010006048B2

(12) United States Patent
Graham et al.

(10) Patent No.: US 10,006,048 B2
(45) Date of Patent: *Jun. 26, 2018

(54) SYNTHETIC GENES AND GENETIC CONSTRUCTS

(71) Applicant: Commonwealth Scientific and Industrial Research Organisation, Acton ACT (AU)

(72) Inventors: Michael Wayne Graham, Jindalee (AU); Robert Norman Rice, Sinnamon Park (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/199,394

(22) Filed: Jun. 30, 2016

(65) Prior Publication Data

US 2017/0002379 A1    Jan. 5, 2017

Related U.S. Application Data

(63) Continuation of application No. 14/688,388, filed on Apr. 16, 2015, now abandoned, which is a continuation of application No. 13/866,238, filed on Apr. 19, 2013, now Pat. No. 9,029,527, which is a continuation of application No. 13/290,609, filed on Nov. 7, 2011, now Pat. No. 8,431,547, which is a continuation of application No. 10/821,726, filed on Apr. 8, 2004, now Pat. No. 8,053,419, which is a continuation of application No. 10/346,853, filed on Jan. 17, 2003, now Pat. No. 8,067,383, which is a continuation of application No. 09/100,812, filed on Jun. 19, 1998, now Pat. No. 6,573,099.

(30) Foreign Application Priority Data

Mar. 20, 1998 (AU) .................................. PP2492

(51) Int. Cl.
| C12N 15/113 | (2010.01) |
| C12N 15/85 | (2006.01) |
| C12N 9/10 | (2006.01) |
| C12N 9/12 | (2006.01) |
| C12N 9/50 | (2006.01) |
| C12N 15/63 | (2006.01) |
| C12N 15/69 | (2006.01) |
| C12N 15/82 | (2006.01) |
| C12N 9/02 | (2006.01) |

(52) U.S. Cl.
CPC ........... *C12N 15/85* (2013.01); *C12N 9/0071* (2013.01); *C12N 9/1051* (2013.01); *C12N 9/127* (2013.01); *C12N 9/503* (2013.01); *C12N 15/113* (2013.01); *C12N 15/63* (2013.01); *C12N 15/69* (2013.01); *C12N 15/8216* (2013.01); *C12N 15/8218* (2013.01); *C12N 15/8283* (2013.01); *C12N 2800/108* (2013.01); *C12N 2830/00* (2013.01); *C12N 2830/002* (2013.01); *C12N 2830/15* (2013.01); *C12N 2830/38* (2013.01); *C12N 2830/42* (2013.01); *C12N 2830/55* (2013.01); *C12N 2830/60* (2013.01); *C12N 2840/102* (2013.01); *C12N 2840/20* (2013.01)

(58) Field of Classification Search
CPC .................................................... C12N 15/113
See application file for complete search history.

(56) References Cited

U.S. PATENT DOCUMENTS

| 6,573,099 | B2 * | 6/2003 | Graham | C12N 9/1051 424/93.2 |
| 7,754,697 | B2 * | 7/2010 | Graham | A61K 48/00 514/44 R |
| 8,053,419 | B2 * | 11/2011 | Graham | C12N 9/1051 514/44 A |
| 8,067,383 | B2 * | 11/2011 | Graham | C12N 9/1051 514/44 R |
| 8,168,774 | B2 * | 5/2012 | Graham | A61K 48/00 536/24.5 |
| 8,431,547 | B2 * | 4/2013 | Graham | C12N 9/1051 514/44 A |
| 9,029,527 | B2 * | 5/2015 | Graham | C12N 9/1051 536/24.5 |

FOREIGN PATENT DOCUMENTS

WO    WO 94/01550    *  1/1994

OTHER PUBLICATIONS

Bi et al. PNAS 93:819-823 1996.*

* cited by examiner

*Primary Examiner* — Brian A Whiteman
(74) *Attorney, Agent, or Firm* — John P. White; Gary J. Gershik; Cooper & Dunham LLP

(57) ABSTRACT

The present invention relates generally to synthetic genes for modifying endogenous gene expression in a cell, tissue or organ of a transgenic organism, in particular a transgenic animal or plant. More particularly, the present invention provides novel synthetic genes and genetic constructs which are capable of repressing delaying or otherwise reducing the expression of an endogenous gene or a target gene in an organism when introduced thereto.

15 Claims, 28 Drawing Sheets

SYNTHETIC GENES AND GENETIC CONSTRUCTS

This application is a continuation of U.S. Ser. No. 14/688,388, filed Apr. 16, 2015, which is a continuation of U.S. Ser. No. 13/866,238, filed Apr. 19, 2013, now U.S. Pat. No. 9,029,527, issued May 12, 2015, which is a continuation of U.S. Ser. No. 13/290,609, filed Nov. 7, 2011, now U.S. Pat. No. 8,431,547, issued Apr. 30, 2013, which is a continuation of U.S. Ser. No. 10/821,726, filed Apr. 8, 2004, now U.S. Pat. No. 8,053,419, issued Nov. 8, 2011, which is a continuation of U.S. Ser. No. 10/346,853, filed Jan. 17, 2003, now U.S. Pat. No. 8,067,383, issued Nov. 29, 2011, which is a continuation of U.S. Ser. No. 09/100,812, filed Jun. 19, 1998, now U.S. Pat. No. 6,573,099 B2, issued Jun. 3, 2003, which claims priority of Australian Provisional Patent Application No. PP2492, filed Mar. 20, 1998, the entire contents of each of which are hereby incorporated by reference into the subject application.

FIELD OF THE INVENTION

The present invention relates generally to synthetic genes for modifying endogenous gene expression in a cell, tissue or organ of a transgenic organism, in particular a transgenic animal or plant. More particularly, the present invention provides novel synthetic genes and genetic constructs which are capable of repressing delaying or otherwise reducing the expression of an endogenous gene or a target gene in an organism when introduced thereto.

This application incorporates-by-reference nucleotide and/or amino acid sequences which are present in the file named "160914_ 0687_ 74768_ A7_SEQUENCELISTING_AWG.TXT", which is 3 kilobytes in size, and which was created Sep. 14, 2016 in the IBM-PC machine format, having an operating system compatibility with MS-Windows, which is contained in the text file filed Sep. 14, 2016 as part of this application.

BACKGROUND TO THE INVENTION

Controlling metabolic pathways in eukaryotic organisms is desirable for the purposes of producing novel traits therein or introducing novel traits into a particular cell, tissue or organ of said organism. Whilst recombinant DNA technology has provided significant progress in an understanding of the mechanisms regulating eukaryotic gene expression, much less progress has been made in the actual manipulation of gene expression to produce novel traits. Moreover, there are only limited means by which human intervention may lead to a repression, delay or reduction in eukaryotic gene expression.

Current methods for down-regulating gene expression, using recombinant DNA technology comprise the introduction of a transgene to the cell which is capable of repressing expression of an endogenous target gene, either transcriptionally or post-transcriptionally. However, the precise mechanism is not known. Moreover, the efficiency of current approaches is low and the results are variable and unpredictable.

Attempts to improve the accuracy and predictability of methods for regulating gene expression in cells, in particular the repression, delay or reduction in expression of viral target genes in eukaryotic cells, foreign transgenes or other foreign genes introduced into cells, tissues or organs by natural means, or endogenous genes which are expressed to produce undesirable traits for a particular purpose, have been largely unsuccessful possibly due to a lack of knowledge of the precise mechanisms involved. As a consequence, the efficiency of methods currently available remains low and highly variable.

In work leading up to the present invention, the inventors sought to elucidate the mechanisms involved in down-regulating gene expression in an attempt to provide improved methods therefor. In so doing the inventors have developed a wide range of synthetic genes capable of modulating gene expression in both prokaryotic and eukaryotic cells and genetic constructs comprising same.

Bibliographic details of the publications referred to by author in this specification are collected at the end of the description. Sequence identity numbers (SEQ ID NOs.) for the nucleotide and amino acid sequences referred to in the specification are defined after the bibliography.

Throughout this specification and the claims that follow, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein, the term "derived from" shall be taken to indicate that a particular integer or group of Integers has originated from the species specified, but has not necessarily been obtained, directly from the specified, source.

SUMMARY OF THE INVENTION

The present invention provides novel synthetic genes and improved genetic constructs comprising same for modifying endogenous or target gene expression in cells, tissues and/or organs which are either transfected or stably transformed therewith.

Accordingly, one aspect of the present invention provides a synthetic gene which is capable of modifying target gene expression in a cell, tissue or organ of a prokaryotic or eukaryotic organism which is transfected or transformed therewith, wherein said synthetic gene at least comprises a structural gene sequence comprising a nucleotide sequence which is substantially identical to the nucleotide sequence of said target gene or a derivative thereof or a complementary sequence thereto placed operably under the control of a promoter sequence which is operable in said cell, tissue or organ.

A further aspect off the invention provides a synthetic gene which is capable of modifying the expression of a target gene in a cell, tissue or organ of a prokaryotic or eukaryotic organism which is transfected or transformed therewith, wherein said synthetic gene at least comprises multiple structural gene sequences, wherein each of said structural gene sequences comprises a nucleotide sequence which is substantially identical to the nucleotide sequence of said target gene or a derivative thereof or a complementary sequence thereto and wherein said multiple structural gene sequences are placed operably under the control of a single promoter sequence which is operable in said cell, tissue or organ.

A third aspect of the present invention provides a synthetic gene which is capable of modifying the expression of a target gene in a cell, tissue or organ of a prokaryote or eukaryote which is transfected or transformed therewith wherein said synthetic gene at least comprises multiple structural gene sequences wherein each of said structural gene sequences is placed operably under the control of a promoter sequence which is operable in said cell, tissue or organ and therein each of said structural gene sequences comprises a nucleotide sequence which is substantially identical to the nucleotide sequence of said target gene or a derivative thereof or a complementary sequence thereto.

A further aspect of the present invention provides a genetic construct which is capable of modifying the expression of an endogenous gene or target gene in a transformed or transfected cell, tissue or organ wherein said genetic construct at least comprises the synthetic gene of the invention and one or more origins of replication and/or selectable marker gene sequences.

A still further aspect of the invention provides a cell, tissue, organ or organism comprising the synthetic genes and genetic constructs described herein.

DETAILED DESCRIPTION OF THE PREFERRED EMBODIMENTS

Figure 1:
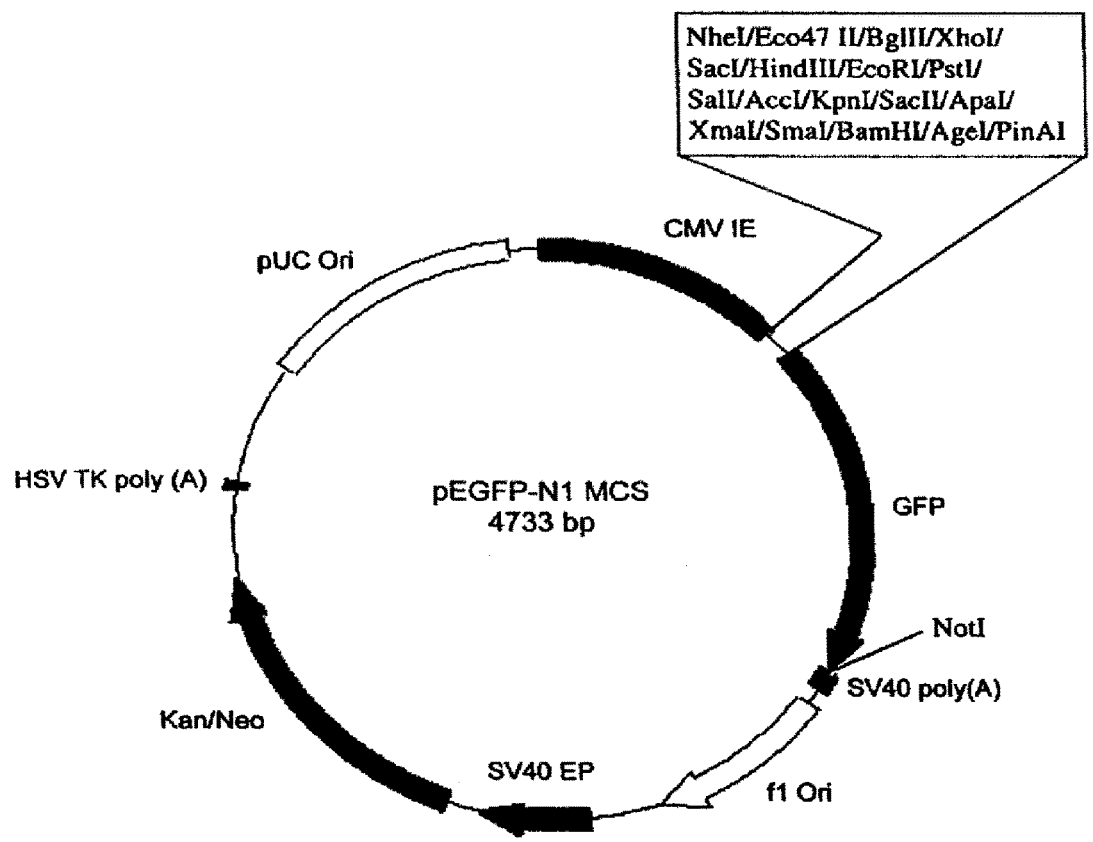
FIG. 1 is a copy of a diagrammatic representation of the plasmid pEGFP-N1 MCS.

One a sped of the present invention provides a synthetic gene which is capable of modifying the expression of a target gene in a cell, tissue or organ wherein said synthetic gene at least comprises a structural gene comprising a nucleotide sequence which is substantially identical to the nucleotide sequence of said target gene or a derivative thereof or a complementary sequence thereto placed operably under the control of a promoter which is operable in said cell, tissue or organ.

Reference herein to a "gene" is to be taken in its broadest context and includes:

(i) a classical genomic gene consisting of transcriptional and/or translational regulatory sequences and/or a coding region and/or non-translated sequences (i.e. introns, 5'- and 3'-untranslated sequences);

(ii) mRNA or cDNA corresponding to the coding regions (i.e. exons) optionally comprising 5'- or 3'-untranslated sequences linked thereto; or (iii) an amplified DNA fragment or other recombinant nucleic add molecule produced in vitro and comprising all or a part of the coding region and/or 5'- or 3'-untranslated sequences linked thereto.

The term "gene" is also used to describe synthetic or fusion molecules encoding all or part of a functional product, in particular a sense or antisense mRNA product or a peptide, oligopeptide or polypeptide or a biologically-active protein.

The term "synthetic gene" refers to a non-naturally occurring gene as hereinbefore defined which preferably comprises at least one or more transcriptional and/or translational regulatory sequences operably linked to a structural gene sequence.

The term "structural gene" shall be taken to refer to a nucleotide sequence which is capable of being transmitted to produce mRNA and optionally, encodes a, peptide, oligopeptide, polypeptide or biologically active protein molecule. Those skilled in the art will be aware that not all mRNA is capable of being translated into a peptide, oligopeptide, polypeptide or protein, for example if the mRNA lacks a functional translation start signal or alternatively, if the mRNA is antisense mRNA. The present invention clearly encompasses synthetic genes comprising nucleotide sequences which are not capable of encoding peptides, oligopeptides, polypeptides or biologically-active proteins. In particular, the present inventors have found that such synthetic genes may be advantageous in modifying target gene expression in cells, tissues or organs of a prokaryotic or eukaryotic organism.

The term "target gene" shall be taken to refer to any gene, the expression of which is to be modified using the synthetic gene of the invention. Preferred target genes include, but are not limited to viral genes and foreign genes which have been introduced into the cell, tissue or organ or alternatively, genes which are endogenous to the cell, tissue or organ.

Wherein, the target gene is a viral gene, it is particularly preferred that the viral gene encodes a function which, is essential for replication or reproduction of the virus, such as but not limited to a DNA polymerase or RNA polymerase gene or a viral coat protein gene, amongst others. In a particularly preferred embodiment, the target gene comprises an RNA polymerase gene derived from a single-stranded (+) RNA virus such as bovine enterovirus (BEV), Sinbis alphavirus or a lentivirus such as, but not limited to, an immunodeficiency virus (eg. HIV-1) or alternatively, a DNA polymerase derived from a double-stranded DNA virus such as bovine herpesvirus or herpes simplex virus I (HSVI), amongst others.

Wherein the target gene is a foreign gene, those skilled in the art will be aware that it will have been introduced to the cell, tissue or organ using transformation technology or alternatively, comprise a gene derived from a pathogen which has been introduced to said cell, tissue or organ by naturally-occurring gene transfer processes.

Particularly preferred foreign target genes include any transgene which has been introduced the cell, tissue or organ.

Wherein the target gene is a gene which is endogenous to the ash, tissue or organ, it is particular preferred that its expression is capable of being monitored by a visual assay, enzyme assay or immunoassay. Particularly preferred endogenous target genes are those detected by visual assay means.

The synthetic genes of the present invention may be derived from naturally-occurring genes by standard recombinant techniques, the only requirement being that the synthetic gene is substantially identical at the nucleotide sequence level to at least a part of the target gene, the expression of which is to be modified. By "substantially identical" is meant that the structural gene sequence of the synthetic gene is at least about 80%-90% identical to 30 or more contiguous nucleotides of the target gene, more preferably at least about 90-95% identical to 30 or more contiguous nucleotides of the target gene and even more preferably at least about 95-99% identical or absolutely identical to 30 or ore contiguous nucleotides of the target gene.

Generally, a gene of the invention may be subjected to mutagenesis to produce single or multiple nucleotide substitutions, deletions and/or additions without affecting its ability to modify target gene expression. Nucleotide insertional derivatives of the synthetic gene of the present invention include 5' and 3' terminal fusions as well as intra-sequence insertions of single or multiple nucleotides. Insertional nucleotide sequence variants are those in which one or more nucleotides are introduced bio a predetermined site in the nucleotide sequence although random insertion is also possible with suitable screening of the resulting product.

Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

Accordingly, the present invention extends to homologues, analogues and derivatives of the synthetic genes described herein.

For the present purpose, "homologues" of a gene as hereinbefore defined or of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a gene as hereinbefore defined or of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic add molecule, for example carbohydrates, radiochemicals including radionucleotides, reporter molecules such as, but not limited to DIG, alkaline phosphatase or horseradish peroxidase, amongst others.

"Derivatives" of a gene as hereinbefore defined or of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

Accordingly, the structural gene component of the synthetic gene may comprise a nucleotide sequence which is at least about 80% identical to at least about 30 contiguous nucleotides of an endogenous target gene, a foreign target gene or a viral target gene present in a cell, tissue or organ or a homologue, analogue, derivative thereof or a complementary sequence thereto.

Preferred structural gene components of the synthetic gene of the invention comprise ax least about 20-30 nucleotides in length derived from a viral DNA polymerase, viral RNA polymerase, viral coat protein or visually-detectable gene, more particularly an RNA polymerase gene derived from a virus selected from the list comprising BEV, Sindbis alphavirus, HIV-1, bovine herpes virus and HSV1 or a visually-detectable gene which is involved in determining pigmentation, cell death or other external phenotype on a cell, tissue, organ or organism, amongst others.

In a particularly preferred embodiment, the structural gene component of the synthetic gene comprises at least about 20-30 nucleotides in length derived from the BEV RNA-dependent RNA polymerase gene or the murine tyrosinase gene or the *Escherichia coli* lac repressor gene lacI or a complementary sequence thereto.

The structural gene component may comprise a nucleotide sequence which encodes an amino acid sequence, with or without a translation start signal (ATG) or a nucleotide sequence which is complementary thereto. Those skilled in the art will be aware that, in the absence of the translation start signal in an appropriate reading frame, the mRNA encoded by the structural gene will not be translated in most eukaryotic and prokaryotic cells.

Alternatively, the structural gene may comprise a nucleotide sequence which does not encode an amino acid sequence or more commonly, comprises one or more open reading frames which encode one or more peptides, oligopeptides or polypeptides which are unrelated at the amino acid sequence level to the amino acid sequence encoded by the target gene. For example, the mRHA product of the structural gene may be inserted into the synthetic gene of the invention so as to alter or disrupt the reading frame of the structural gene and produce one or more frame shift mutations in the translation product thereof relative to the translation product encoded by the target gene, notwithstanding a substantial identity between die structural gene and the target gene on the one hand and the corresponding mRNA products of the structural gene and the target gene on the other hand. Such effects may be produced by introducing one or two nucleotide substitutions or deletions into the structural gene, relative to the target gene sequence or alternatively, by introducing a translation start codon 5'-ATG-3' upstream of any nucleotide in the structural gene which occurs at a particular position in a codon of the corresponding target gene such that the position of said nucleotide in the codon of the structural gene is altered.

Alternatively, the structural gene may encode no amino acid sequence or one or more amino acid sequences which are unrelated, to the amino acid sequence encoded by the target gene wherein said structural gene is transcribed in the antisense orientation from the synthetic gene promoter, relative to the direction of transcription of the corresponding target gene. In such circumstances, the mRNA product of the structural gene will comprise a nucleotide sequence which is complementary to the nucleotide sequence in the corresponding region of the mRNA encoded by the target gene.

The present invention clearly encompasses synthetic genes wherein the structural gene component is operably connected in the sense or antisense orientation to a promoter sequence and irrespective of the capacity of said structural gene to encode an amino acid sequence which is encoded by the target gene. Accordingly, the structural gene component may further comprise 5'-untranslated region and/or 3'-untranslated region and/or intron (eg. SV40 intron) and/or a coding region derived from the target gene or a complementary nucleotide sequence thereto.

Reference herein to a "promoter" is to be taken in its broadest context and includes the transcriptional regulatory sequences of a classical genomic gene, including the TATA box which is required for accurate transcription initiation in eukaryotic cells, with or without a CCAAT box sequence and additional regulatory elements (i.e. upstream activating sequences, enhancers and silencers). For expression in prokaryotic cells, such as bacteria, the promoter should at least contain the −35 box and −10 box sequences.

A promoter is usually, but not necessarily, positioned upstream or 5', of the structural gene component of the synthetic gene of the invention, the expression of which it regulates. Furthermore, the regulatory elements comprising a promoter are usually positioned within 2 kb of the start site of transcription of the structural gene.

In the present context, the term "promoter" is also used to describe a synthetic or fusion, molecule, or derivative which confers, activates or enhances expression of an isolated nucleic acid molecule, in a cell, such as a plant, animal, insect, fungal, yeast or bacterial cell. Preferred promoters may contain additional copies of one or more specific regulatory elements, to further enhance expression of a structural gene which expression it regulates and/or to alter the spatial expression and/or temporal expression of same. For example, regulatory elements which confer inducibility on the expression of the structural gene may be placed adjacent to a heterologous promoter sequence driving expression of a nucleic acid molecule.

Placing a structural gene under the regulatory control of a promoter sequence means positioning said molecule such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation to this distance can also occur.

Examples of promoters suitable for use in the synthetic gates of the present invention include viral, fungal, bacterial, animal and plant derived promoters capable of functioning in plant, animal, insect, fungal, yeast or bacterial cells. The promoter may regulate the expression of the structural gene component constitutively, or differentially with respect to cell, the tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a eukaryotic cell, tissue or organ, at least during the period of time over which the target gene is expressed therein and mote preferably also immediately preceding the commencement of detectable expression of title target gene in said cell, tissue or organ.

Accordingly, strong constitutive promoters are particularly preferred for the purposes of the present invention or promoters which may be induced by virus infection or the commencement of target gene expression.

Examples of preferred promoters include the bacteriophage T7 promoter, bacteriophage T3 promoter, SP6 promoter, lac operator-promoter, tac promoter, SV40 late promoter, SV40 early promoter. RSV-LTR promoter, CMV IE promoter and the like.

Particularly preferred promoters contemplated herein include promoters operable in eukaryotic cells, for example the SV40 early promoter, SV40 late promoter or the CMV IE promoter sequence. Those skilled in the an will readily be aware of additional promoter sequences other than those specifically described.

In the present context, the terms "in operable connection with" or "operably under the control" or similar shall be taken to indicate that expression of the structural gene is under the control of the promoter sequence with which it is spatially connected; in a cell, tissue, organ or whole organism.

In a more particularly preferred embodiment of the invention, the synthetic gene according to this aspect of the invention comprises the coding region of the BEV polymerase gene placed in the sense orientation operably under the control of the CMV IE promoter or SV40 late promoter. In an alternative embodiment, the synthetic gene comprises a nucleotide sequence derived from the coding region of the BEV polymerase gene but lacking a translation—start site, placed in the sense orientation in operable connection with the CMV IE promoter or SV40 late promoter. In a further alternative embodiment, the synthetic gene comprises a nucleotide sequence derived from the BEV polymerase gene placed in the antisense orientation relative to the BEV polymerase gene and in operable connection with the CMV IE promoter or the SV40 late promoter sequence.

For the present purposes, the term "BEV polymerase" as used herein shall be taken to refer to a structural gene, cDNA molecule, genomic gene or nucleotide sequence al least about 30-50 nucleotides in length which is derived from the nucleotide sequence of the bovine enterovirus (BEV) RNA-dependent RNA polymerase gene, including both translatable and non-translatable nucleotide sequences and nucleotide sequences which are complementary to a part of the nucleotide sequence of the full-length BEV RNA-dependent RNA polymerase gene.

In a further alternative embodiment, the synthetic gene according to this aspect of the invention comprises the coding region of a tyrosinase gene, in particular the murine tyrosinase gene, placed in the sense orientation operably under the control of the CMV IE promoter or SV40 late promoter. As with other embodiments described herein, the synthetic gene (i.e. tyrosinase gene) may lack a functional translation start site or be introduced in the antisense orientation. The present invention clearly encompasses all such embodiments.

As used herein, the term "tyrosinase gene" shall be taken to refer to a structural gene, cDNA molecule, genomic gene or nucleotide sequence which is capable of encoding the tyrosinase enzyme or a polypeptide fragment thereof or alternatively, a nucleotide sequence which is complementary to said structural gene, cDNA molecule, genomic gene or nucleotide sequence. Particularly preferred tyrosinase genes for use in the performance of the present invention include, but are not limited to, those described by Kwon et al (1988) and homologues, analogues and derivatives thereof and complementary nucleotide sequences thereto.

In still a further alternative embodiment, the synthetic gene according to this aspect of the invention comprises the coding region of the lacI gene, placed in the sense orientation operably under the control of the CMV IE promoter or SV40 late promoter. As with other embodiments described herein, the synthetic gene (i.e. *E. coli* lacI gene) may lack a functional translation start site or be introduced in the antisense orientation. The present invention clearly encompasses all such embodiments.

As used herein, the term "lacI gene" shall be taken to refer to a structural gene, cDNA molecule, genomic gene or nucleotide sequence which is capable of encoding a polypeptide repressor of the lacZ gene which encodes the enzyme β-galactosidase or alternatively, a nucleotide sequence which is complementary to said structural gene, cDNA molecule, genomic gene or nucleotide sequence. Those skilled in the art will be aware that the lac repressor is a DNA-binding protein which acts on the lac operator-promoter sequence. In the presence of one of a variety of β-galactosides, the affinity of the lac repressor for the lac operator-promoter sequence is lowered, thereby allowing RNA polymerase to bind the lac operator-promoter region to activate transcription of the lac operon.

Standard methods may be used to produce the structural genes of the present invention, in particular the BEV polymerase and tyrosinase genes which are derived from publicly available material. For example, the BEV polymerase aid tyrosinase genes may be amplified using the polymerase chain reaction or alternatively, isolated using standard hybridisation techniques known to those skilled in the art.

For the purposes of nomenclature, the nucleotide sequence of the cDNA encoding murine tyrosinase is publicly available under GenBank Accession No. M20234.

A second aspect of the present invention provides a synthetic gene which is capable of modifying the expression of a target gene in a cell, tissue or organ, wherein said synthetic gene at least comprises multiple structural gene sequences wherein each of said structural gene sequences comprises a nucleotide sequence which is substantially identical to the nucleotide sequence of the target gene or a derivative thereof or a complementary sequence thereto and wherein said multiple structural gene sequences are placed operably under the control of a single promoter sequence which is operable in said cell, tissue or organ.

As used herein, the term "multiple structural gene sequences" or similar term shall be taken to refer to any number of structural genes as defined herein which is greater than or equal to two. Accordingly, a multiple structural gene sequence may comprise a tandem repeat or concatemer of two or more identical nucleotide sequences or alternatively, a tandem array or concatemer of non-identical nucleotide sequences, the only requirement being that each of the structural gene sequences contained therein is substantially identical to the target gene sequence or a complementary sequence thereto. In this regard, those skilled in the art will be aware that a cDNA molecule may also be regarded as a multiple structural gene sequence in the context of the present invention, in so far as it comprises a tandem array or concatemer of exon sequences derived from a genomic target gene. Accordingly, cDNA molecules and any tandem array, tandem repeat or concatemer of exon sequences and/or intron sequences and/or 5'-untranslated and/or 3'-untranslated sequences are clearly encompassed by this embodiment of the invention.

Preferably, the multiple structural gene comprises at least 2-4 individual structural gene sequences, more preferably at least about 4-6 individual structural gene sequences and more preferably at least about 6-8 individual structural gene sequences.

The optimum number of structural gene sequences which may be involved in the synthetic gene of the present invention will vary considerably, depending upon the length of each of said structural gene sequences, their orientation and degree of identity to each other. For example, those skilled in the art will be aware of the inherent instability of palindromic nucleotide sequences in vivo and the difficulties associated with constructing long synthetic genes comprising inverted repeated nucleotide sequences, because of the tendency for such sequences to form hairpin loops and to recombine in vivo. Notwithstanding such difficulties, the optimum number of structural gene sequences to be included in the synthetic genes of the present invention may be determined empirically by those skilled in the art, without any undue experimentation and by following standard procedures such as the construction of the synthetic gene of the invention using recombinase-deficient cell lines, reducing the number of repeated sequences to a level which eliminates or minimises recombination events and by keeping the total length of the multiple structural gene sequence to an acceptable limit, preferably no more than 5-10 kb, more preferably so more than 2-5 kb and even more preferably no more than 0.5-2.0 kb in length.

In an alternative embodiment, each structural gene contained within the multiple structural gene unit of the subject synthetic gene may comprise a nucleotide sequence which is substantially identical to a different target gene in the same organism. Such an arrangement may be of particular utility when the synthetic gene is intended to provide protection against a pathogen in a cell, tissue or organ, in particular a viral pathogen, by modifying the expression of viral target genes. For example, the multiple structural gene may comprise nucleotide sequences which are substantially identical to two or more target genes selected from the list comprising DNA polymerase, RNA polymerase and coat protein or other target gene which is essential for viral infectivity, replication or reproduction. However, it is preferred with this arrangement that the structural gene units are selected such that the target genes to which they are substantially identical are normally expressed at approximately the same time (or later) in an infected cell, tissue or organ as (than) the multiple structural gene of the subject synthetic gene is expressed under control of the promoter sequence. This means that the promoter controlling expression of the multiple structural gene will usually be selected to confer expression in the cell, tissue or organ over the entire life cycle of the virus when the viral target genes are expressed at different stages of infection.

The individual structural gene units of the multiple structural gene according to the embodiments described herein may be spatially connected in any orientation relative to each other, for example head-to-head, head-to-tail or tail-to-tail and all such configurations are within the scope of the invention.

Preferably, the multiple structural gene unit comprises two structural genes in a head-to-tail or head-to-head configuration. More preferably, the multiple structural gene unit comprises two identical or substantially identical structural genes or a homologue, analogue or derivative thereof in a head-to-tail configuration as a direct repeat or alternatively, in a head-to-head configuration as an inverted repeat or palindrome.

In a particularly preferred embodiment, the multiple structural gene unit comprises two identical or substantially identical structural genes comprising nucleotide sequences derived from the BEV polymerase or tyrosinase gene or a homologue, analogue or derivative thereof, placed in a head-to-head or head-to-tail configuration.

According to this aspect of the invention, wherein the multiple structural gene or any individual structural gene unit thereof is intended to be both transcribed and translated, a translation start signal nay be included at the 5' end of that open reading frame. In a particularly preferred embodiment, the structural gene unit which is positioned nearer the 5' end of the synthetic gene comprises an in-frame translation start signal of facilitate translation of the first open reading frame of the multiple structural gene in a cell, tissue or organ into which the synthetic gene is introduced. Those skilled in the art will be aware that it is also possible to produce a fusion polypeptide from such an arrangement provided that the individual structural gene units are positioned such that their open reading frames are in-frame with respect to each other or alternatively, the individual structural gene units are separated by intron/exon splice boundary sequences such that splicing of the mRNA product of the synthetic gene produces a translatable mRNA wherein the said open reading frames are in-frame with respect to each other. Such embodiments are clearly contemplated by the present invention. Intron/exon splice junction sequences are well-known in the art and the skilled person would readily be able to introduce such sequences to the 5'- and 3'-ends of a structural gene unit of the synthetic genes described herein.

The individual structural genes comprising the multiple structural gene unit may be further spatially separated by the addition of a linker molecule or "stuffer fragment" there between. The stuffer fragment may comprise any combination of nucleotide or amino acid residues, carbohydrate molecules or oligosaccharide molecules or carbon atoms or a homologue, analogue or derivative thereof which is capable of being linked covalently to a nucleic acid molecule.

Preferably, embodiment, the stuffer fragment comprises a sequence of nucleotides or a homologue, analogue or derivative thereof.

More preferably, the stuffer fragment comprises a sequence of nucleotides of at least about 10-50 nucleotides in length, even more preferably at least about 50-100 nucleotides in length and still more preferably at least about 100-500 nucleotides in length.

Wherein the multiple structural gene unit comprises intron/exon splice junction sequences, the stuffer fragment may serve as an intern sequence placed between the 3'-splice site of the structural gene nearer the 5'-end of the gene and the 5'-splice site of the next downstream structural gene. Alternatively, wherein it is desirable for more than two adjacent structural genes to be translated, the stuffer fragment placed there between should not include an in-frame translation stop codon, absent intron/exon splice junction sequences at both ends of the stuffer fragment or the addition of a translation start codon at the 5' end of each structural gene unit, as will be obvious to those skilled in the art.

Preferred stuffer fragments are those which encode detectable marker proteins or biologically-active analogues and derivatives thereof, for example luciferase, β-galacturonase, β-galactosidase, chloramphenicol acetyltransferase or green fluorescent protein, amongst others.

According to this embodiment, the detectable marker or an analogue or derivative thereof serves to indicate the expression of the synthetic gene of the invention in a cell, tissue or organ by virtue of its ability to confer a specific detectable phenotype thereon, preferably a visually-detectable phenotype.

In a more particularly preferred embodiment of the invention, the multiple structural gene comprises an interrupted direct repeat or interrupted palindrome comprising two identical or substantially-identical BEV polymerase structural gene sequences or alternatively, two identical or substantially-identical tyrosinase structural gene sequences or a homologue, analogue or derivative thereof separated by a stuffer fragment comprising a nucleotide sequence which encodes green-fluorescent protein or a biologically-active analogue or derivative thereof.

As used herein, the term "green fluorescent protein" or "GFP" shall be taken to refer to a protein, polypeptide or peptide which is capable of producing a strong green fluorescence when excited with near ultraviolet radiation or blue light or a homologue, analogue or derivative thereof. Accordingly, the term "GFP gene" shall be taken to refer to a nucleotide sequence which is capable of encoding GFP or a complementary nucleotide sequence thereto. Particularly preferred GFPs and GFP genes according to the present invention are derived from the jellyfish *Aequoria victoria* as described by Prasher et at (1992) or in International Patent Publication No. WO 95/07463, amongst others.

A further aspect of the invention provides for each structural gene of the multiple structural gene unit to be placed operably under the control of a separate promoter sequence.

According to this embodiment, the promoters controlling expression of the structural gene unit are preferably different promoter sequences, to reduce competition there between for cellular transcription factors and RNA polymerases. Preferred promoters are selected from those referred to supra.

Those skilled in the art will know how to modify the arrangement or configuration of the individual structural genes as described supra to regulate their expression from separate promoter sequences.

In a particularly preferred embodiment, the multiple structural gene unit comprises two or more BEV polymerase structural genes or two or more tyrosinase structural genes wherein each of said structural genes is placed operably in connection with a different promoter sequence. More particularly preferred, the multiple structural gene unit comprises two BEV polymerase structural genes or two tyrosinase structural genes positioned as inverted repeats or direct repeats wherein one of said structural genes is placed operably in connection with the CMV IE promoter. Even more preferably, at least one of the BEV polymerase structural genes or tyrosinase genes comprising the multiple structural gene is presented in the sense orientation and comprises a translation start signal to facilitate translation of mRNA encoded therefrom.

Those skilled in the art will be aware that the structural genes comprising the multiple structural gene unit according to this aspect of the invention are expressed as physically-distinct mRNA species and, as a consequence, wherein said mRNA species are translated, no fusion polypeptide will be produced there between. However, the present invention clearly extends to synthetic gene which comprises two or more structural genes operably connected to a first promoter sequence and one or more structural genes operably connected to one or more additional promoter sequences.

The synthetic genes described supra are capable of being modified further, for example by the inclusion of marker nucleotide sequences encoding a detectable marker enzyme or a functional analogue or derivative thereof, to facilitate detection of the synthetic gene in a cell, tissue or organ in which it is expressed. According to this embodiment, the marker nucleotide sequences will be present in a translatable format and expressed, for example as a fusion polypeptide with the translation product(s) of any one or more of the structural genes or alternatively as a non-fusion polypeptide.

Alternatively or in addition, the synthetic genes described supra may further comprise one or more transcription termination sequences placed at the 3'-end of the transcriptional unit of the synthetic gene sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the synthetic genes of the present invention include the SV40 polyadenylation signal, the HSV TK polyadenylation signal, the CYC1 terminator, ADH terminator, SPA terminator, nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit gene (SSU) gene terminator sequences, subclover stunt virus (SCSV) gene sequence terminators, any rho-independent *E. coli* terminator, or the lacZ alpha terminator, amongst others.

In a particularly preferred embodiment, the terminator is the SV40 polyadenylation signal or the HSV TK polyadenylation signal which are operable in animal cells, tissues and organs or the lacZ alpha terminator which is active in prokaryotic cells.

Those skilled in the art will be aware of additional promoter sequences and terminator sequences which may be suitable for use in performing the invention. Such sequences may readily be used without any undue experimentation.

The synthetic genes of the present invention may be introduced to a suitable cell, tissue or organ without modification as linear DNA in the form of a genetic construct, optionally contained within a suitable carrier, such as a cell, virus particle or liposome, amongst otters. To produce a genetic construct, the synthetic gene of the invention is inserted into a suitable vector or episome molecule, such as a bacteriophage vector, viral vector or a plasmid, cosmid or artificial chromosome vector which is capable of being maintained and/or replicated and/or expressed in the host cell, tissue or organ into which it is subsequently introduced.

Accordingly a further aspect of the invention provides a genetic construct which at least comprises the synthetic gene according to any one or more of the embodiments described herein and one or more origins of replication and/or selectable marker gene sequences.

Usually, an origin of replication or a selectable marker gene suitable for use in bacteria is physically-separated from those genetic sequences contained in the genetic construct which are intended to be expressed or transferred to a eukaryotic cell, or integrated into the genome of a eukaryotic cell.

In a particularly preferred embodiment, the origin of replication is functional in a bacterial cell and comprises the pUC or the ColE1 origin or alternatively the origin of replication is operable in a eukaryotic cell, tissue and more preferably comprises the 2 micron (2 μm) origin of replication or the SV40 origin of replication.

As used herein, the term "selectable marker gene" include any gene which confers a phenotype on a cell in which it is expressed to facilitate the identification and/or selection of cells which are transfected or transformed with a genetic construct of the invention or a derivative thereof.

Suitable selectable marker genes contemplated herein include the ampicillin-resistance gene (Amp$^r$), tetracycline-resistance gene (Tc$^r$), bacterial kanamycin-resistance gene (Kan$^r$), is the zeocin resistance gene (Zeocin is a drug of bleomycin family which is trademark of InVitrogen Corporation), the AURI-C gene which confers resistance to the antibiotic aureobasidin A, phosphinothricin-resistance gene, neomycin phosphotransferase gene (npfII), hygromycin-resistance gene, β-glucuronidase (GUS) gene, chloramphenicol acetyltransferase (CAT) gene, green fluorescent protein-encoding gene or the luciferase gene, amongst others.

Preferably, the selectable marker gene is the nptII gene or Kan$^r$ gene or green fluorescent protein (GFP)-encoding gene.

Those skilled in the art will be aware of other selectable marker genes useful in the performance of the present invention and the subject invention is not limited by the nature of the selectable marker gene.

The present invention extends to all genetic constructs essentially as defined herein, which include further genetic sequences intended for the maintenance and/or replication of said genetic construct in prokaryotes and/or the integration of said genetic construct or a part thereof into the genome of a eukaryotic cell or organism.

The present invention further extends to an isolated cell, tissue or organ comprising the synthetic gene described herein or a genetic construct comprising same. Any standard means may be used for their introduction including cell mating, transformation or transfection procedures known to those skilled in the art or described by Ausubel et al (1992).

The present invention is further described by reference to the following non-limiting Examples.

EXAMPLE 1

Base Plasmids

Plasmid pEGFP-N1 MCS

Plasmid pEGFP-N1 MCS (FIG. 1; Clontech) contains the CMV IE promoter operably connected to an open reading frame encoding a red-shifted variant of wild-type green fluorescent protein (GFP; Prasher et al, 1992; Chalfie et al., 1994; Inouye and Tsuji, 1994), which has been optimised for brighter fluorescence. The specific GFP variant encoded by pEGFP-N1 MCS has been disclosed by Cormack et al. (1996). Plasmid pEGFP-N1 MCS contains a multiple cloning site comprising BglII and BamHI sites and many other restriction endonuclease cleavage sites, located between the CMV IE promoter and the GFP open reading frame. Structural genes cloned into the multiple cloning site will be expressed at the transcriptional level if they lack a functional translation start site, however such structural gene sequences will not be expressed at the protein level (i.e. translated). Structural gene sequences inserted into the multiple cloning site which comprise a functional translation start site will be expressed as GFP fusion polypeptides if they are cloned in-frame with the GFP-encoding sequence. The plasmid further comprises an SV40 polyadenylation signal downstream of the GFP open reading frame to direct proper processing of the 3'-end of mRNA transcribed from the CMV-IE promoter sequence. The plasmid further comprises the SV40 origin of replication functional in animal cells; the neomycin-resistance gene comprising SV40 early promoter (SV40 EP in FIG. 1) operably connected to the neomycin/temamycin-resistance gene derived from Tr5 (Kan/neo in FIG. 1) and the HSV thymidine kinase polyadenylation signal (HSV TK poly (A) in FIG. 1), for selection of transformed cells on kamanycin, neomycin or G418; the pUC19 origin of replication which is functional in bacterial cells (pUC Ori in FIG. 1); and the f1 origin of replication for single-stranded DNA production (f1 Ori in FIG. 1).

pCMVLacI

Plasmid pCMVLacI is a commercially-obtainable mammalian expression vector (Stratagene) comprising the lacI gene encoding the lac repressor and a gene coding for hygromycin resistance (Hyg$^r$).

Plasmid pOPRSVI/MCS

Plasmid pOPRSVI/MCS is a commercially-obtainable mammalian expression vector (Stratagene), comprising the OPRSV1 promoter sequence (a modified RSV-LTR promoter), SV40 intron sequence, lac operator sequence, multiple cloning site and thymidine kinase (TK) gene transcription terminator sequence [i.e. TK poly(A) signal].

Plasmid pSVL

Plasmid pSVL is commercially-obtainable from Pharmacia and serves as a source of the SV40 late promoter sequence. The nucleotide sequence of pSVL is also publicly available as GenBank Accession Number U13868.

Plasmid pCMV.cass

Plasmid pCMV.cass (FIG. 2) is an expression cassette for driving expression of a structural gene sequence under control of the CMV-IE promoter sequence. Plasmid pCMV.cass was derived from pEGFP-N1 MCS by deletion of the GFP open reading frame as follows: Plasmid pEGFP-N1 MCS was digested with PinAI and Not I, blunt-ended using PfuI polymerase and then re-ligated. Structural gene sequences are cloned into pCMV.cass using the multiple cloning site, which is identical to the multiple cloning site of pEGFP-N1 MCS, except it lacks the PinAI site.

Plasmid pCR2.1

Plasmid pCR2.1 is commercially available from Stratagene and comprises the lacZ promoter sequence and lacZ-α transcription terminator, with a cloning site for the insertion of structural gene sequences there between. Plasmid pCR2.1 is designed to clone nucleic acid fragments by virtue of the A-overhang frequently synthesized by Taq polymerase during the polymerase chain reaction. The plasmid further comprises the ColE1 and f1 origins of replication and kanamycin-resistance and ampicillin-resistance genes.

Plasmid pCR.Bgl-GFP-Bam

Figure 3:
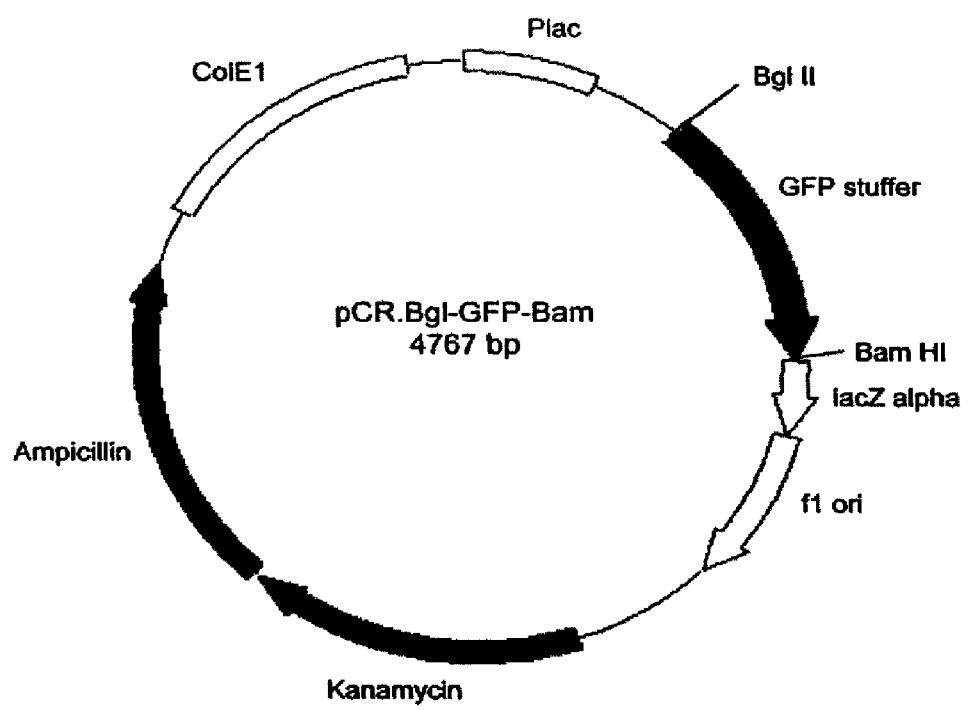
FIG. 3 is a copy of a diagrammatic representation of the plasmid pCR.Bgl-GFP-Bam.

Plasmid pCR.Bgl-GFP-Bam (FIG. 3) comprises an internal region of the GFP open reading frame derived from plasmid pEGFP-N1 MCS (FIG. 1) placed operably under the control of the lacZ promoter. To produce this plasmid, a region of the GFP open reading frame was amplified from pEGFP-N1 MCS using the amplification primers Bgl-GFP (SEQ ID NO:5) and GFP-Bam (SEQ ID NO:6) and cloned into plasmid pCR2.1. The Internal GFP-encoding region in plasmid pCR.Bgl-GFP-Bam lacks functional translational start and stop codons.

Plasmid pCR-SV40L

Figure 4:
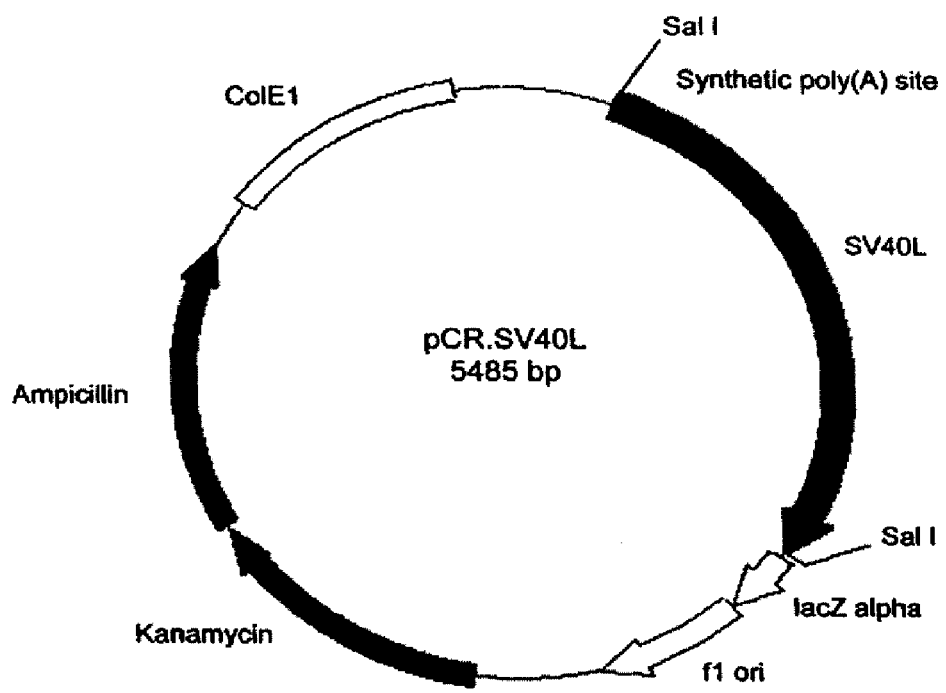
FIG. 4 is a copy of a diagrammatic representation of the plasmid pCR.SV40L.

Plasmid pCR.SV40L (FIG. 4) comprises the SV40 late promoter derived from plasmid pSVL (GenBank Accession No. U13868; Pharmacia), cloned into pCR2.1 (Stratagene). To produce this plasmid, the SV40 late promoter was amplified using the primers SV40-1 (SEQ ID NO:7) and SV40-2 (SEQ ID NO: 8) which comprise Sal I cloning sites to facilitate sub-cloning of the amplified DNA fragment into pCMV.cass. SEQ ID No. 7 also contains a synthetic poly (A) site at the 5' end, such that the amplification product comprises the synthetic poly(A) site at the 5' end of the SV40 promoter sequence.

Plasmid pCMV.SV40L.cass

Figure 5:
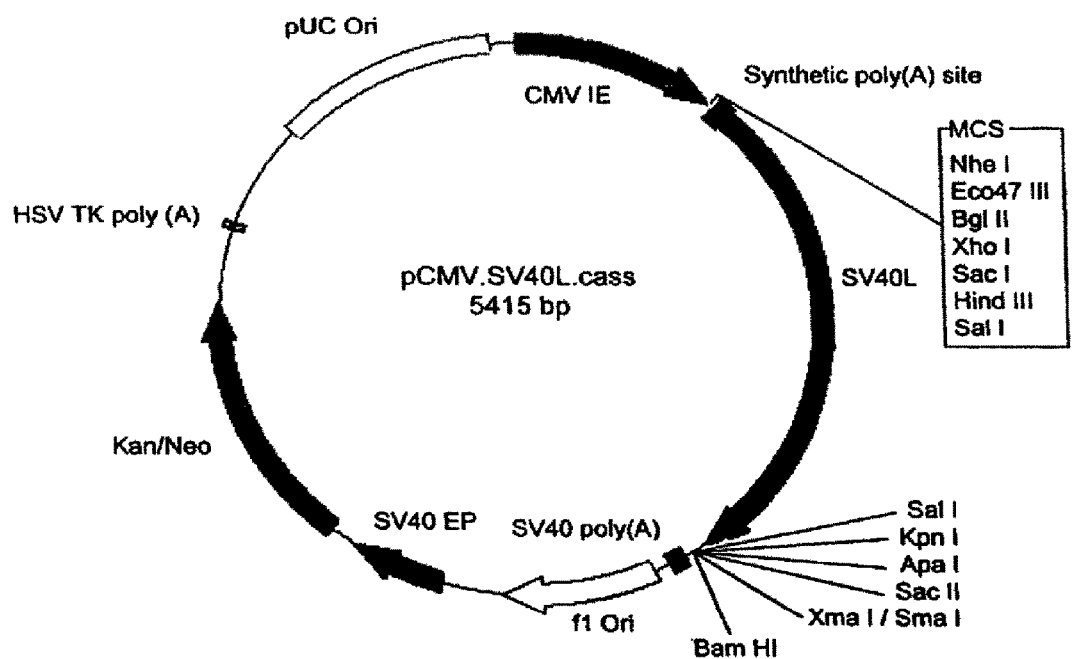
FIG. 5 is a copy of a diagrammatic representation of the plasmid pCMV.SV40L.cass.

Plasmid pCMV.SV40L.cass (FIG. 5) comprises the synthetic poly A site and the SV40 late promoter sequence from plasmid pCR.SV40L (FIG. 4), sub-cloned as a Sal I fragment, into the Sal I site of plasmid pCMV.cass (FIG. 2), such that the CMV-IE promoter and SV40 late promoter sequences are capable of directing transcription in the same direction. Accordingly, the synthetic poly(A) site at the 5' end of the SV40 promoter sequence is used as a transcription terminator for structural genes expressed from the CMV IE promoter in this plasmid, which also provides for the insertion of said structural gene via the multiple cloning site present between the SV40 late promoter and the synthetic poly(A) site (FIG. 5). The multiple cloning sites are located behind the CMV-IE and SV40 late promoters, including BamHI AND BGLII SITES.

EXAMPLE 2

BEV Polymerase-Containing Genes

Plasmid pCR.BEV.1

The BEV RNA-dependent RNA polymerase coding region was amplified as a 1.385 bp DNA fragment from a full-length cDNA clone encoding same, using the primers designated BEV-1 (SEQ ID NO:1) and BEV-2 (SEQ ID NO:2), under standard amplification conditions. The amplified DMA contained a 5'-BglII restriction enzyme site, derived from the BEV-1 primer sequence and a 3'BamHI restriction enzyme site, derived from the BEV-2 primer sequence. Additionally, as the BEV-1 primer sequence contains a translation start signal 5'-ATG-3' engineered at positions 15-17 of SEQ ID NO: 1, the amplified BEV polymerase structural gene comprises the start site in-frame with BEV polymerase-encoding nucleotide-sequences, Thus, the amplified BEV polymerase structural gene comprises the ATG start codon immediately upstream (ie. juxtaposed) to the BEV polymerase-encoding sequence. There Is no translation stop codon in the amplified DNA.

Figure 6:
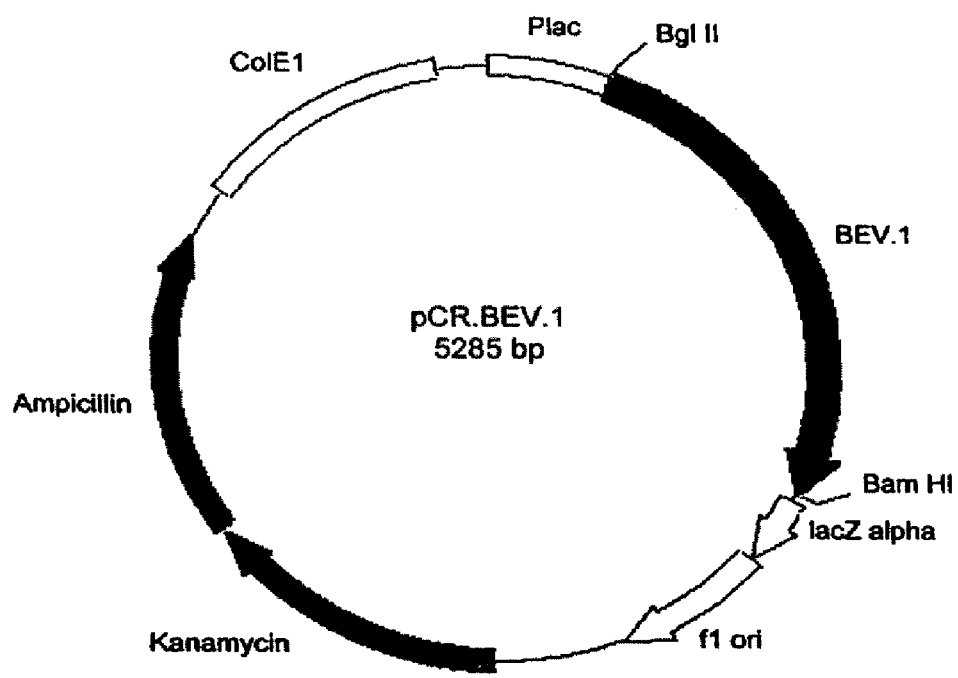
FIG. 6 is a copy of a diagrammatic representation of the plasmid pCR.BEV.1.

The amplified BEV polymerase structural gene was cloned into plasmid pCR2.1 to produce pCR.BEV.1 (FIG. 6).

Plasmid pCR.BEV.2

Figure 7:
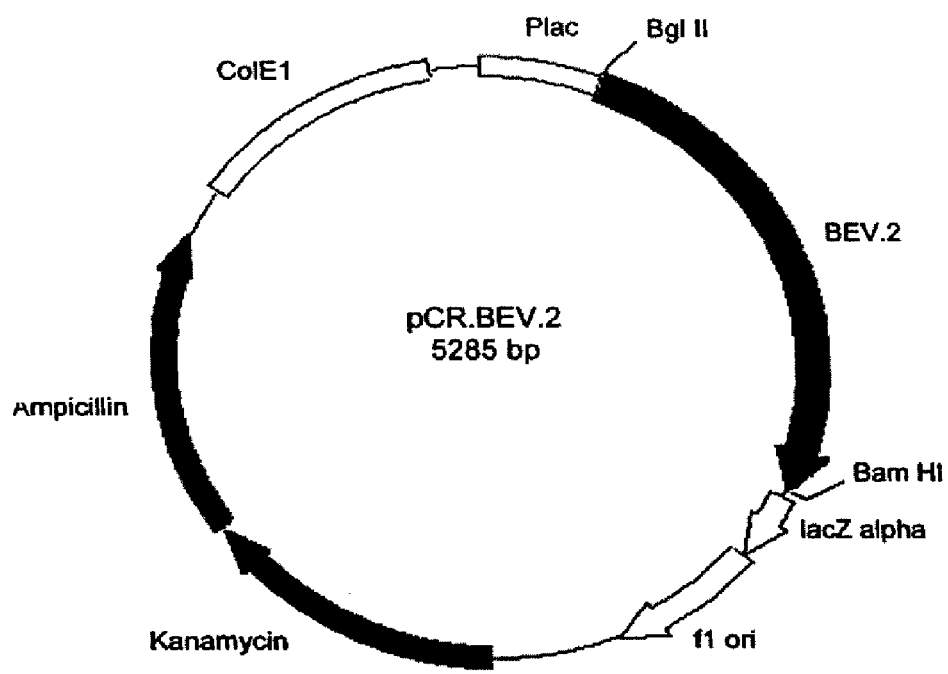
FIG. 7 is a copy of a diagrammatic representation of the plasmid pCR.BEV.2.

The complete BEV polymerase coding region was amplified from a full-length cDNA clone encoding same, using primers BEV-1 (SEQ ID NO: 1) and BEV-3 (SEQ ID NO:3). Primer BEV-3 comprises a BamHI restriction enzyme site at positions 5 to 10 inclusive of SEQ ID NO:3 and the complement of a translation stop signal at positions 11 to 13 of SEQ ID NO: 3. As a consequence, an open reading frame comprising a translation start signal and translation stop signal, contained between the Bgl II and BamHI restriction sites. The amplified fragment was cloned into pCR2.1 to produce plasmid pCR2.BEV.2 (FIG. 7).

Plasmid pCR.BEV.3

Figure 8:
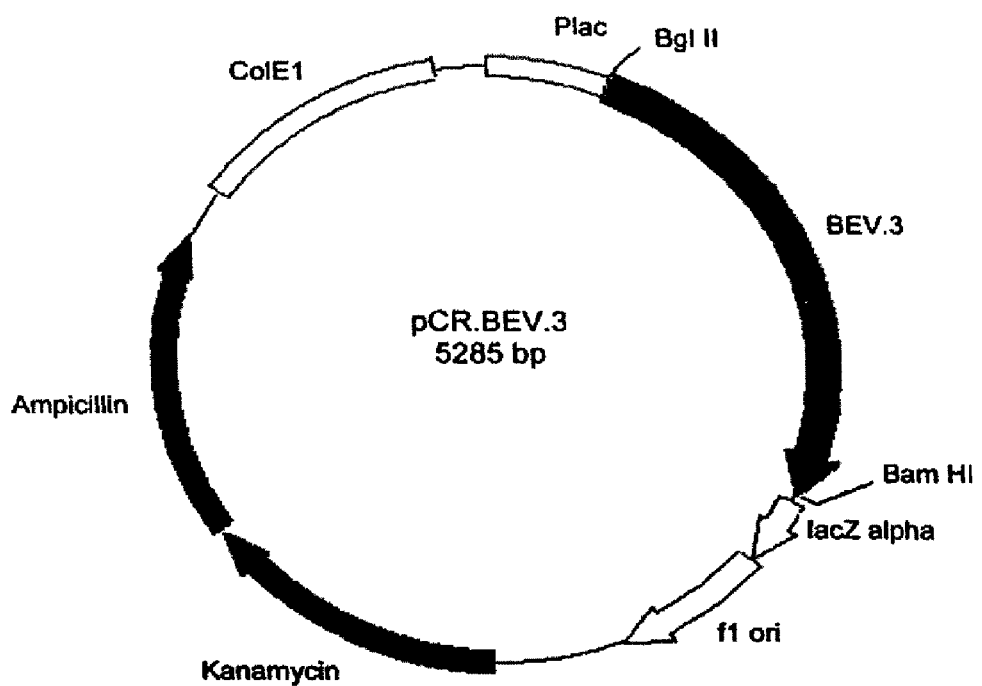
FIG. 8 is a copy of a diagrammatic representation of the plasmid pCR.BEV.3.

A non-translatable BEV polymerase structural Rene was amplified from a full-length BEV polymerase cDNA clone using the amplification primers BEV-3 (SEQ ID NO:3) and BEV-4 (SEQ ID NO:4). Primer BEV-4 comprises a BglII cloning site at positions 5-10 of SEQ ID NO:4 and sequences downstream of this BglII site are homologous to nucleotide sequences of the BEV polymerase gene. There is no functional ATG start codon in the amplified DNA product of primers BEV-3 and BEV-4. The BEV polymerase is expressed as part of a polyprotein and, as a consequence, there is no ATG translation start site in this gene. The amplified DNA was cloned into plasmid pCR2.1 to yield plasmid pCR.BEV.3 (FIG. 8).

EXAMPLE 3

Synthetic Genes Comprising a BEV Polymerase Structural Gene Operably Connected to the CMV-IE Promoter Sequence Plasmid pEGFP.BEV.1

Figure 9:
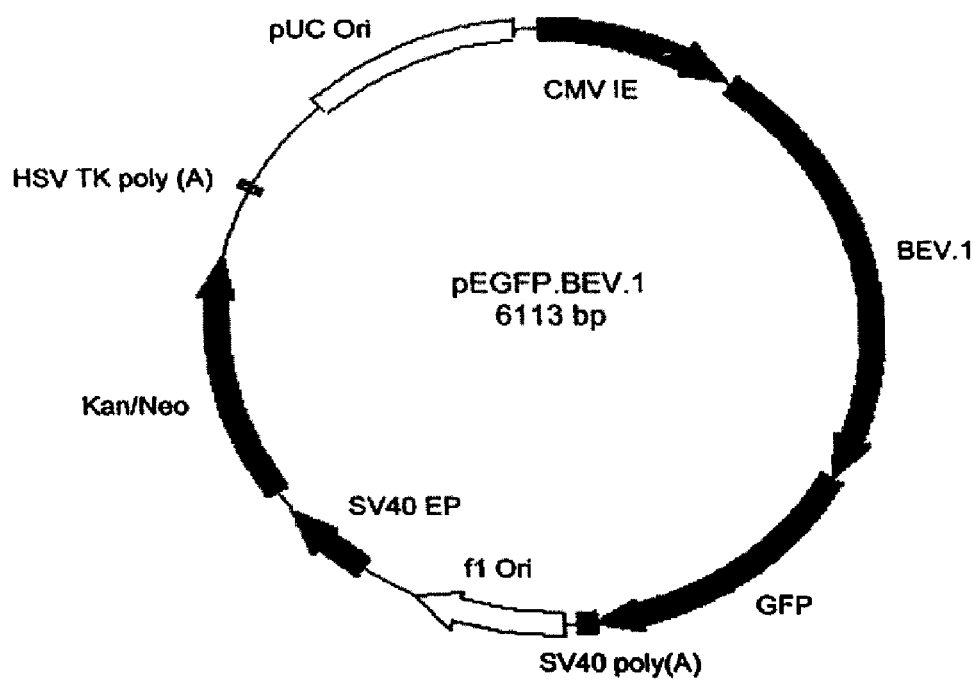
FIG. 9 is a copy of a diagrammatic representation of the plasmid pEGFP.BEV.1.

Plasmid pEGFP.BEV.1 (FIG. 9) is capable of expressing the BEV polymerase structural gene as a GFP fusion polypeptide under the control of the CMV-IE promoter sequence. To produce plasmid pEGFP.BEV.1, the BEV polymerase sequence from pCR.BEV.1 (FIG. 6) was cloned as a BglII-to-BamHI fragment into BglII/BamHI-digested pEGFP-N1 MCS (FIG. 1).

Plasmid pCMV.BEV.2

Figure 2:
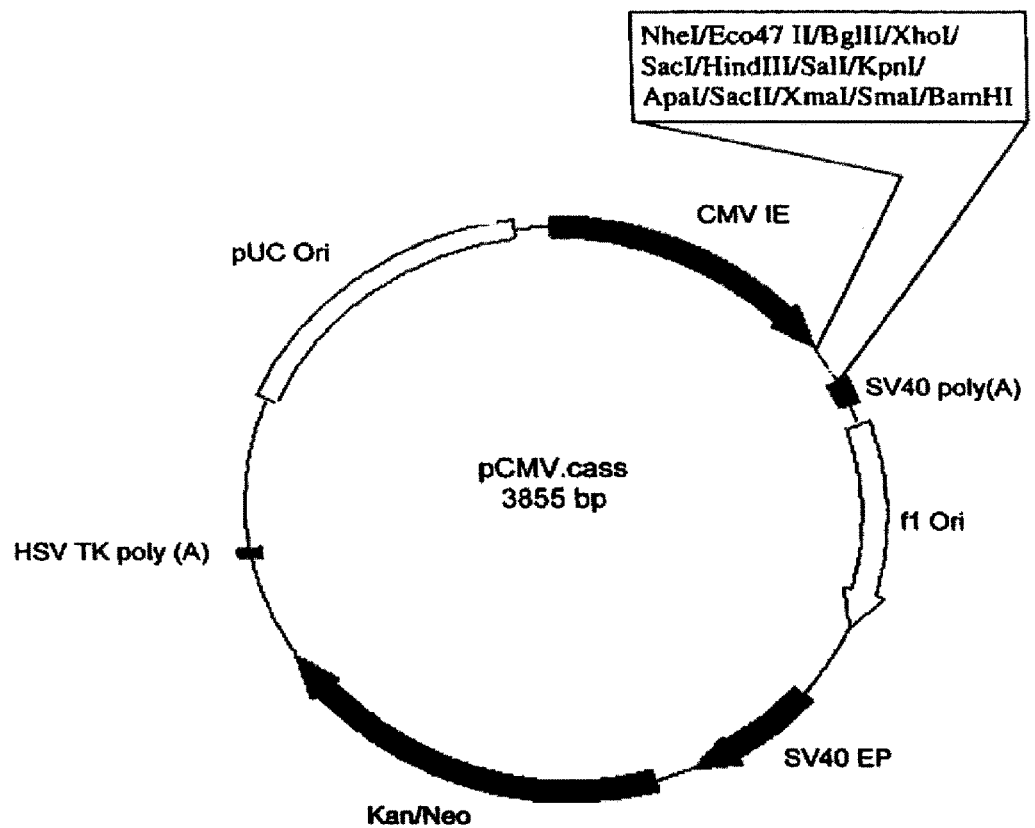
FIG. 2 is a copy of a diagrammatic representation of the plasmid pCMV.cass.
Figure 10:
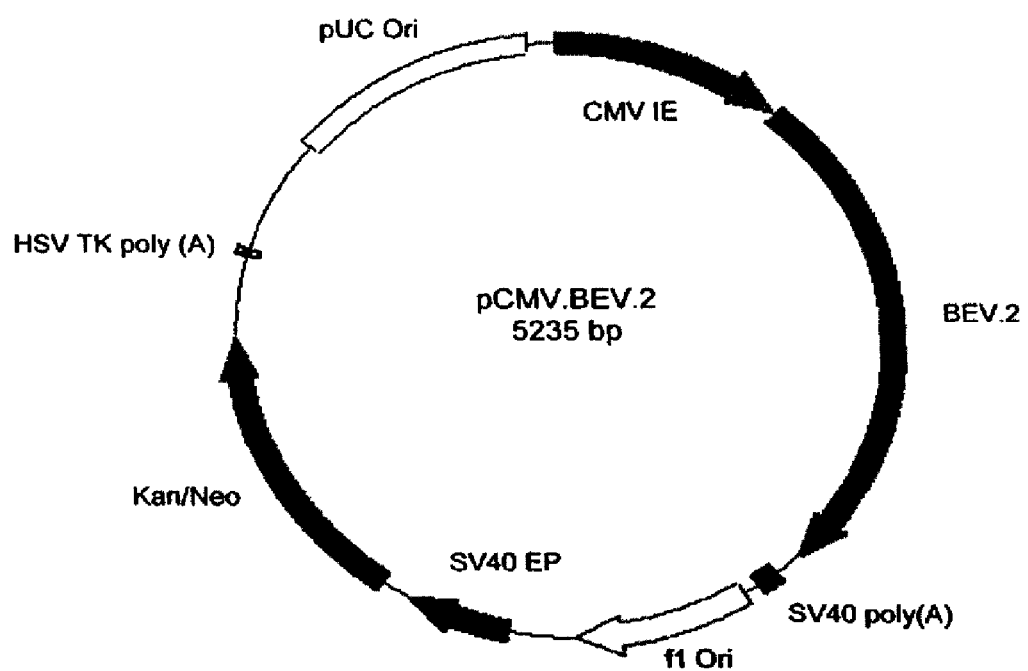
FIG. 10 is a copy of a diagrammatic representation of the plasmid pCMV.BEV.2.

Plasmid pCMV.BEV.2 (FIG. 10) is capable of expressing the entire BEV polymerase open reading frame under the control of CMV-IE promoter sequence. To produce pCMV.BEV.2, the BEV polymerase sequence from pCR.BEV.2 (FIG. 7) was sub-cloned in the sense orientation as a BglII-to-BamHI fragment into BglII/BamHI-digested pCMV.cass (FIG. 2).

Plasmid pCMV.VEB

Figure 11:
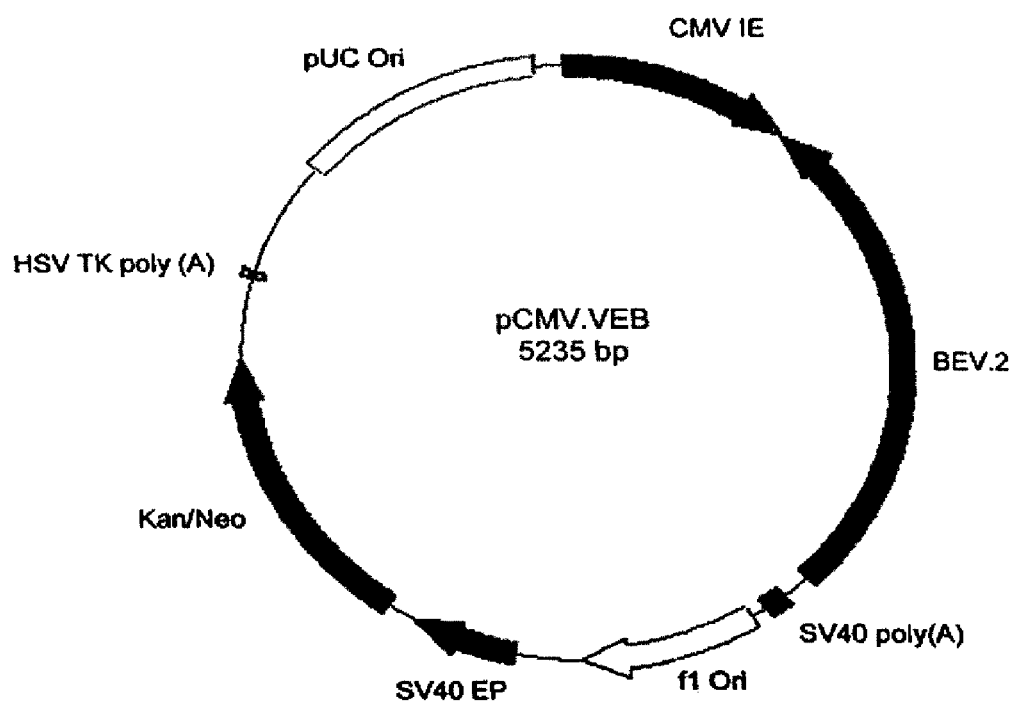
FIG. 11 is a copy of a diagrammatic representation of the plasmid pCMV.VEB.

Plasmid pCMV.VEB (FIG. 11) expresses an antisense BEV polymerase mRNA under die control of the CMV-IE promoter sequence. To produce plasmid pCMV.VEB, the BEV polymerase sequence from pCR.BEV.2 (FIG. 7) was sub-cloned in the antisense orientation as a BglII-to-BamHI fragment into BglII/BamHI-digested pCMV.cass (FIG. 2).

Plasmid pCMV.BEVnt

Figure 12:
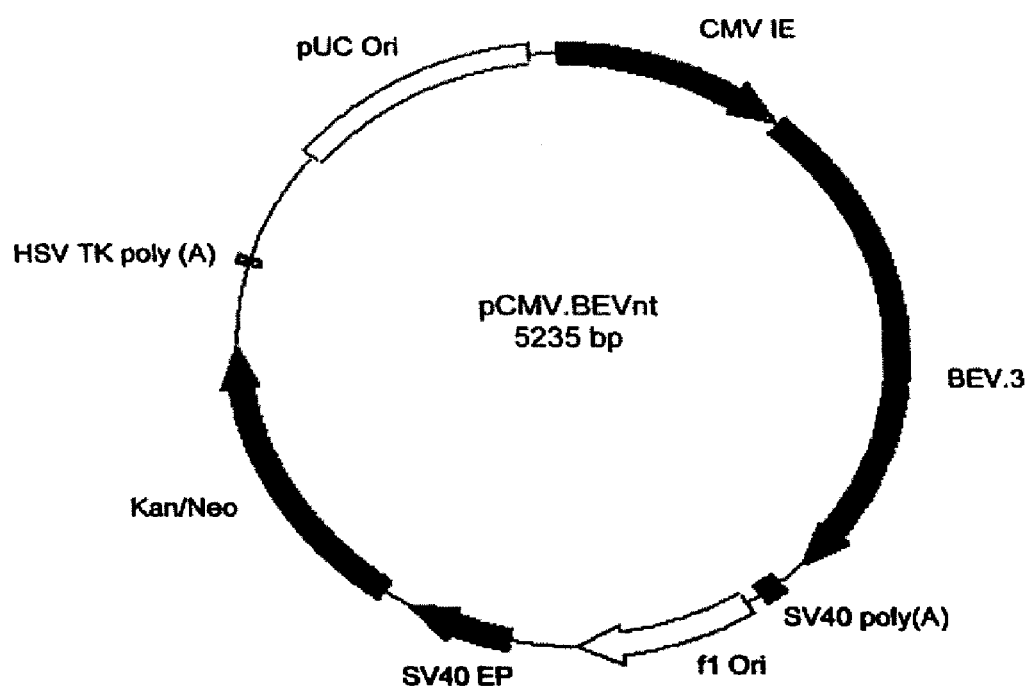
FIG. 12 is a copy of a diagrammatic representation of the plasmid pCMV.BEVnt.

Plasmid pCMV.BEVnt (FIG. 12) expresses a non-translatable BEV polymerase structural gene in the sense orientation under the control of the CMV-IE promoter sequence. To produce pCMV.BEVnt, the BEV polymerase sequence from pCR.BEV.3 (FIG. 8) was sub-cloned in the sense orientation as a BglII-to-BamHI fragment into BglII/BamHI-digested pCMV.cass (FIG. 2).

Plasmid pCMV.BEVx2

Figure 13:
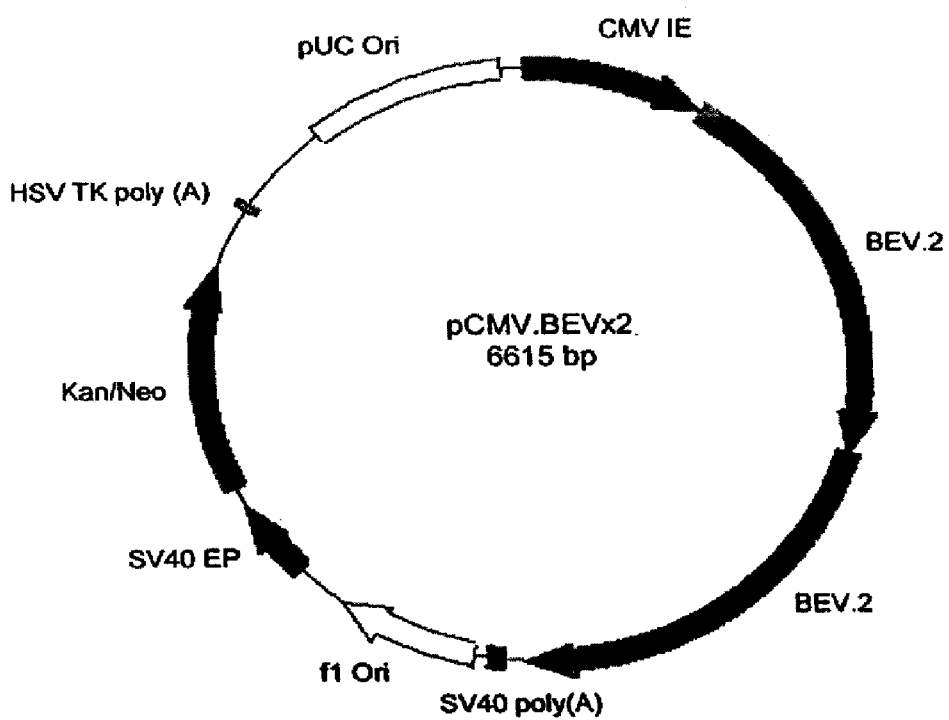
FIG. 13 is a copy of a diagrammatic representation of the plasmid pCMV.BEVx2.

Plasmid pCMV.BEVx2 (FIG. 13) comprises a direct repeat of a complete BEV polymerase open reading frame under the control of the CMV-EE promoter sequence. In eukaryotic cells at least, the open reading frame located nearer the CMV-IE promoter is translatable. To produce pCMV.BEVx2, the BEV polymerase structural gene from plasmid pCR.BEV.2 (FIG. 7) was sub-cloned in the sense orientation as a BglII-to-BamHI fragment into BamHI-digested pCMV.BEV.2 (FIG. 10), immediately downstream of the BEV polymerase structural gene already present therein.

Plasmid pCMV.BEV.VEB

Figure 14:
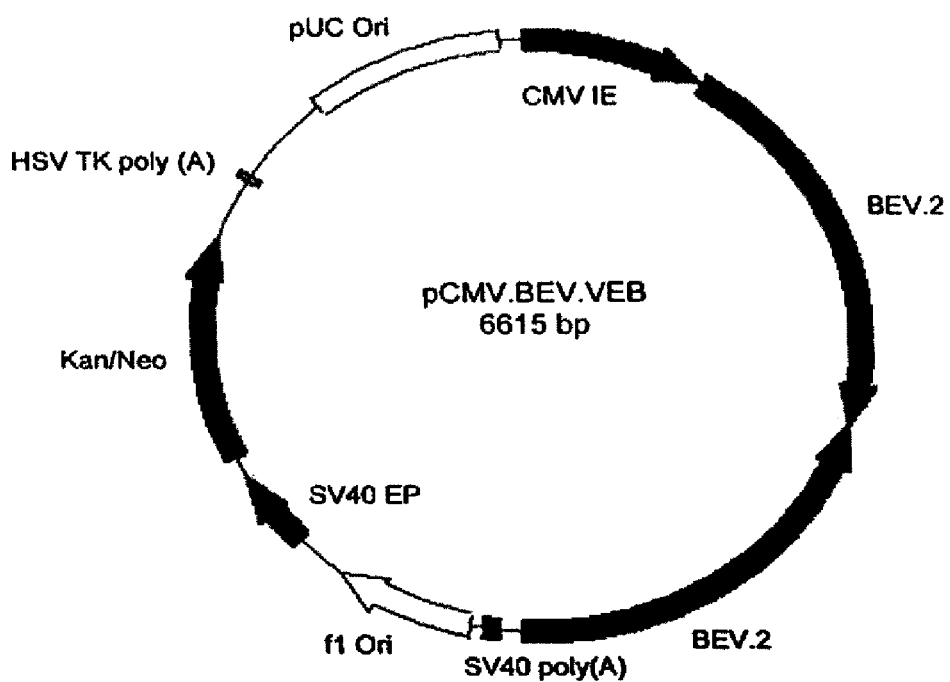
FIG. 14 is a copy of a diagrammatic representation of the plasmid pCMV.BEV.VEB.

Plasmid pCMV.BEV.VEB (FIG. 14) comprises an inverted repeat or palindrome of a complete BEV polymerase open reading frame under the control of the CMV-IE promoter sequence. In eukaryotic cells at least, the open reading frame located nearer, the CMV-IE promoter is translatable. To produce pCMV-BEV.VEB, the BEV polymerase structural gene from plasmid pCR.BEV.2 (FIG. 7) was sub-cloned in the antisense orientation as a BglII-to-BamHI fragment into BamHI-digested pCMV.BEV.2 (FIG. 10), immediately downstream of the BEV polymerase structural gene already present therein.

Plasmid pCMV.BEV.GFP.VEB

Figure 15:
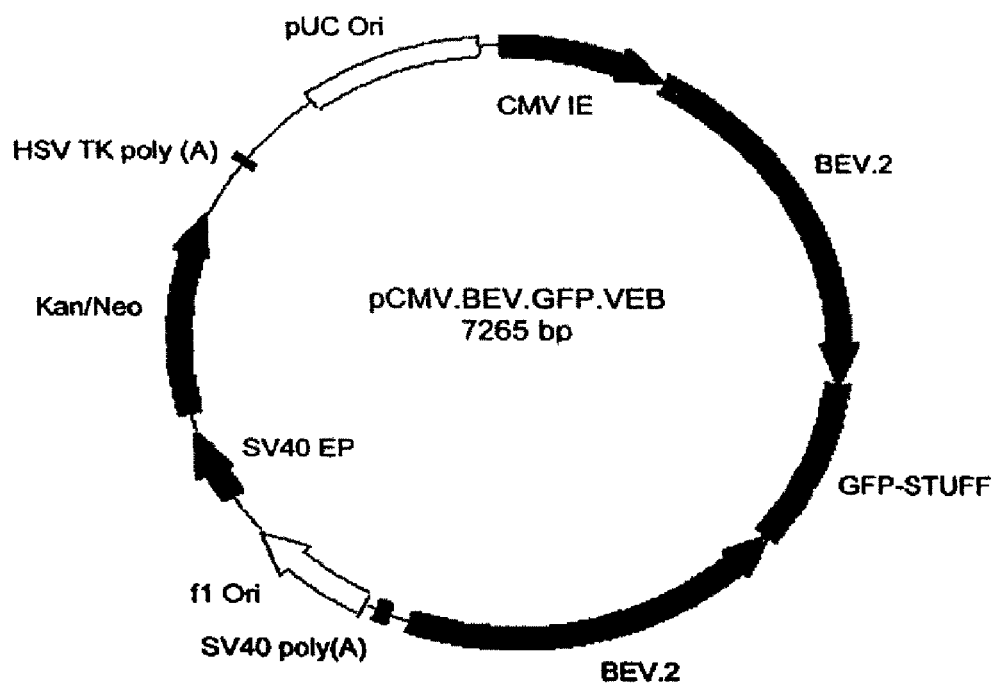
FIG. 15 is a copy of a diagrammatic representation of the plasmid pCMV.BEV.GFP.VEB.

Plasmid pCMV.BEV.GFP.VEB (FIG. 15) is similar to plasmid pCMV.BEV.VEB except that the BEV structural gene inverted repeat or palindrome is interrupted by the insertion of a GFP open reading frame (stuffer fragment) therein. To produce plasmid pCMV.BEV.GFP.VEB, the GFP stuffer fragment from pCR.Bgl-GFP-Bam (FIG. 3) was first sub-cloned in the sense orientation as a BglII-to-BamHI fragment into BamHI-digested pCMV.BEV.2 (FIG. 7) to produce an intermediate plasmid pCMV.BEV.GFP wherein the BEV polymerase-encoding and GFP-encoding sequences are contained within the same 5'-BglII-to-BamHI-3' fragment. The BEV polymerase structural gene from pCMV.BEV.2 (FIG. 7) was then cloned in the antisense orientation as a BglII-to-BamHI fragment into BamHI-digested pCMV.BEV.GFP. The BEV polymerase structural gene nearer the CMV-IE promoter sequence in plasmid pCMV.BEV.GFP.VEB is capable of being translated, at least in eukaryotic cells.

EXAMPLE 4

Figure 16:
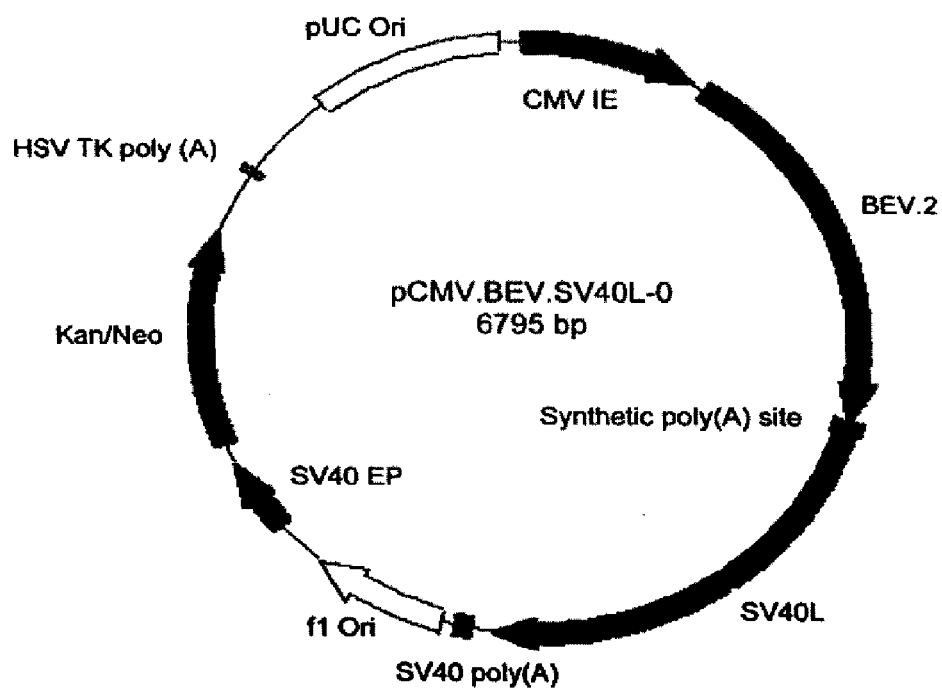
FIG. 16 is a copy of a diagrammatic representation of the plasmid pCMV.BEV.SV40L-O.
Figure 17:
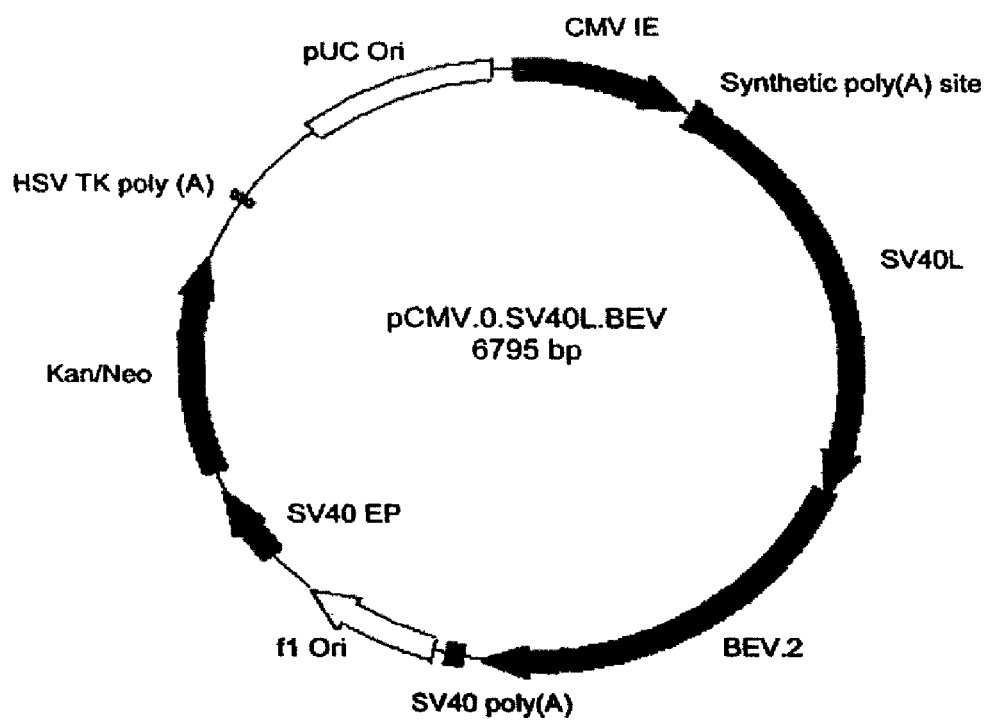
FIG. 17 is a copy of a diagrammatic representation of the plasmid pCMV.0.SV40L.BEV.
Figure 18:
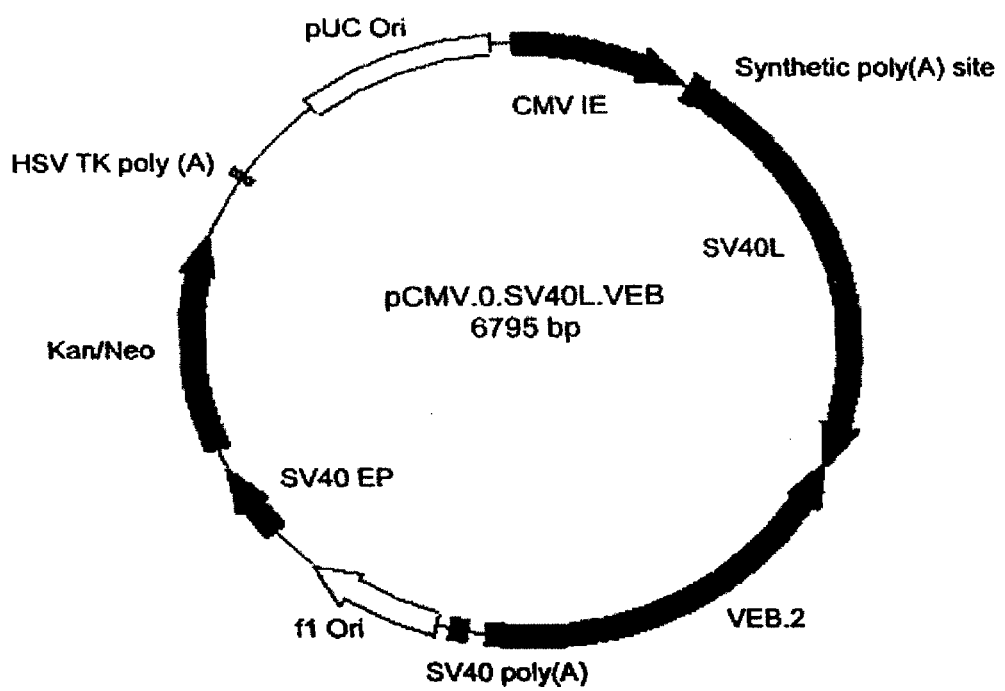
FIG. 18 is a copy of a diagrammatic representation of the plasmid pCMV.0.SV40L.VEB.
Figure 19:
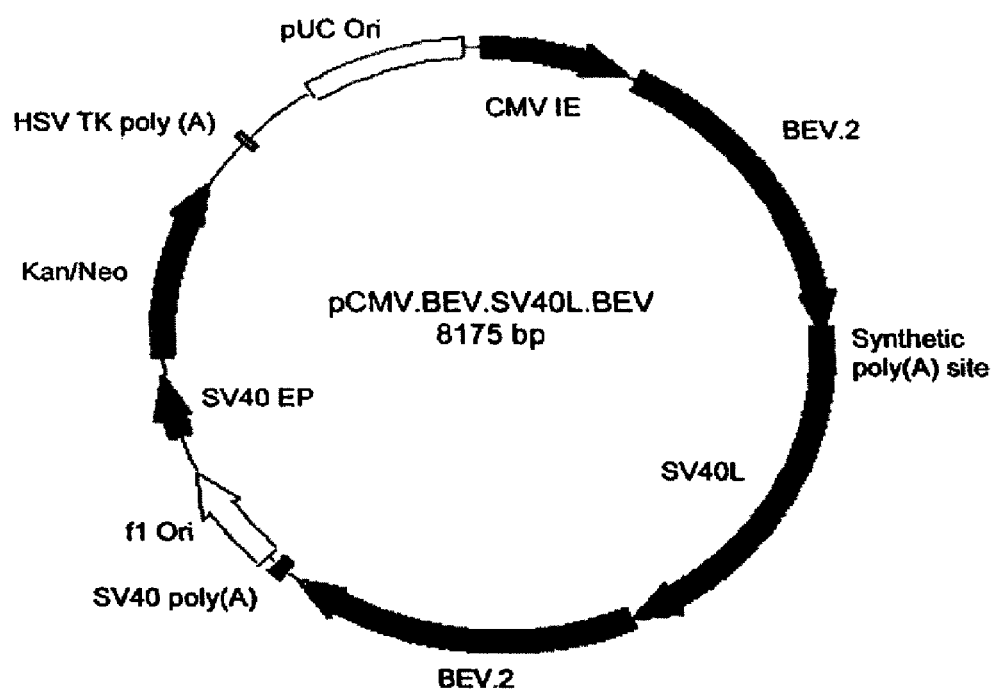
FIG. 19 is a copy of a diagrammatic representation of the plasmid pCMV.BEV.SV40L.BEV.
Figure 20:
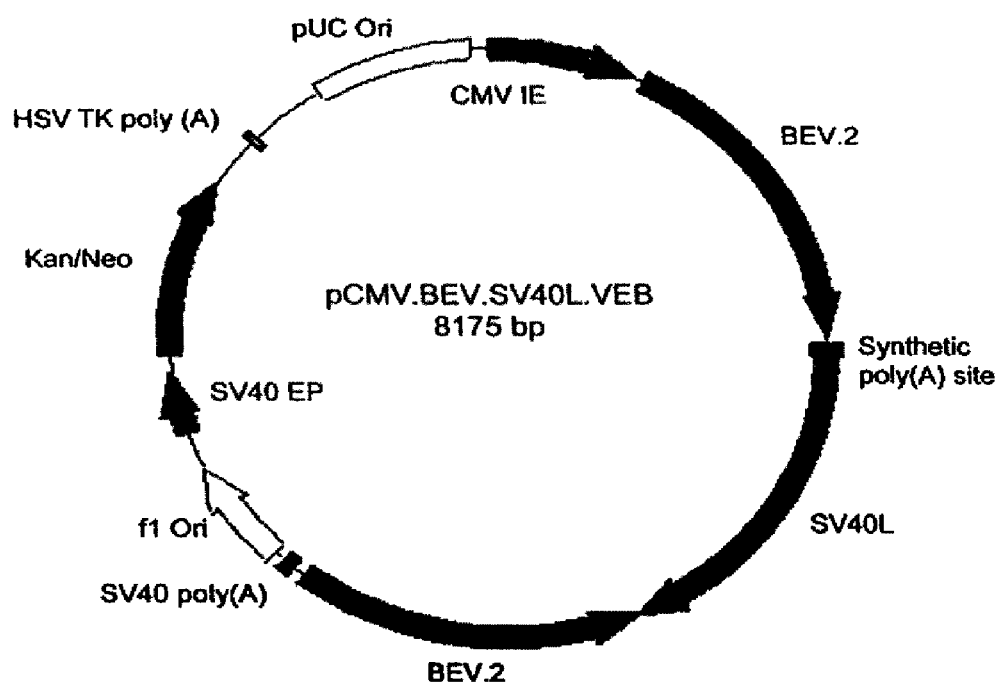
FIG. 20 is a copy of a diagrammatic representation of the plasmid pCMV.BEV.SV40L.VEB.
Figure 21:
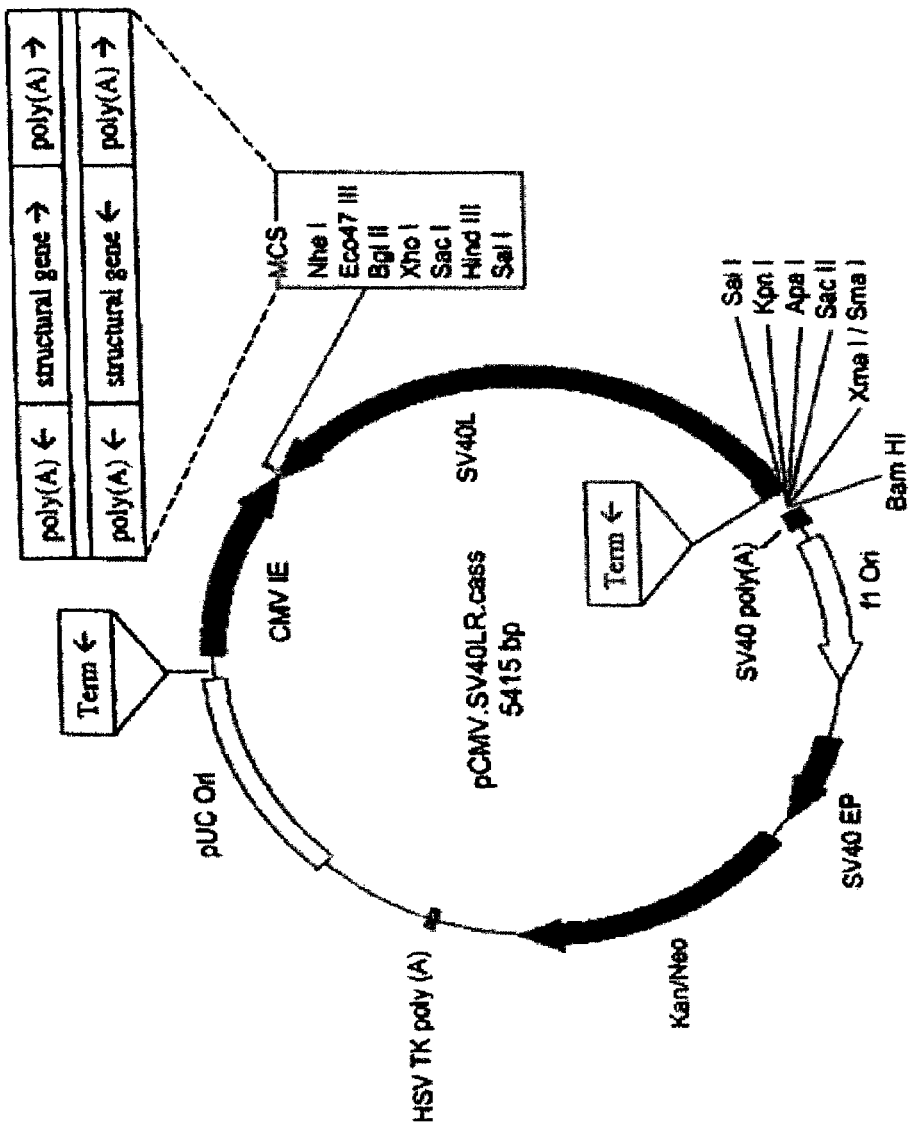
FIG. 21 is a copy of a diagrammatic representation of the plasmid pCMV.SV40LR.cass.
Figure 22:
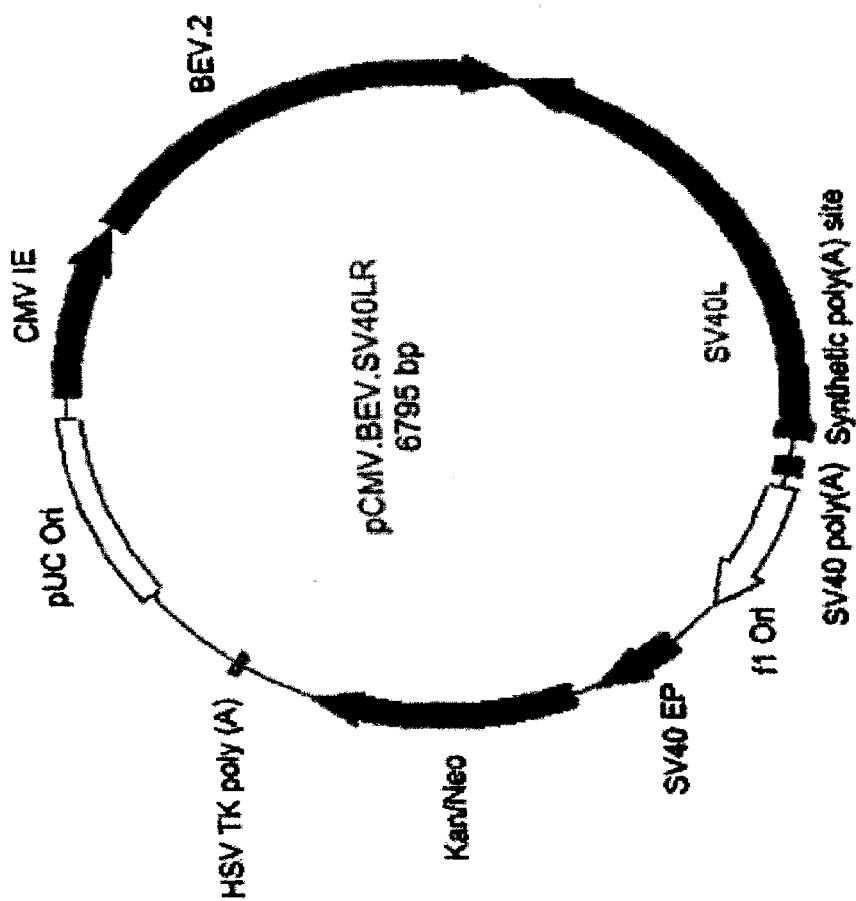
FIG. 22 is a copy of a diagrammatic representation of the plasmid pCMV.BEV.SV40LR.

Synthetic Genes Comprising BEV Polymerase Structural Genes Operably Connected to Multiple Promoter Sequences Plasmid pCMV.BEV.SV40L-O Plasmid pCMV.BEV.SV40L-O (FIG. 16) comprises a translatable BEV polymerase structural gene derived from plasmid pCR.BEV.2 (FIG. 7) inserted in the sense orientation between the CMV-IE promoter and the SV40 late promoter sequences, of plasmid pCMV.SV40L.cass (FIG. 5). To produce plasmid pCMV.BEV.SV40L-O, the BEV polymerase structural gene was sub-cloned as a BglII-to-BamHI fragment into BglII-digested pCMV.SV40L.cass DNA.

Plasmid pCMV.O.SV40L.BEV

Plasmid pCMV.O.SV40L.BEV (FIG. 1) comprises a translatable BEV polymerase structural gene derived from plasmid pCR.BEV.2 (FIG. 7) cloned downstream of tandem CMV-IE promoter and SV40 late promoter sequences present in plasmid pCMV.SV40L.cass (FIG. 5). To produce plasmid pCMV.O.SV40L.BEV, the BEV polymerase structural gene was sub-cloned in the sense orientation as a BglII-to-BamHI fragment into BamHI-digested pCMV.SV40L.cass DNA.

Plasmid pCMV.O.SV40L.VEB

Plasmid pCMV.O.SV40L.VEB (FIG. 18) comprises an antisense BEV polymerase structural gene derived from plasmid pCR.BEV.2 (FIG. 7) cloned downstream of tandem CMV-IE promoter and SV40 late promoter sequences present in plasmid pCMV.SV40L.cass (FIG. 5). To produce plasmid pCMV.O.SV40L.VEB, the BEV polymerase structural gene was sub-cloned in the antisense orientation as a BglII-to-BamHI fragment into BamHI-digested pCMV.SV40L.cass DNA.

Plasmid pCMV.BEV.SV40L.BEV

Plasmid pCMV.BEV.SV40L.BEV (FIG. 19) comprises a multiple structural gene unit comprising two BEV polymerase structural genes placed operably and separately under control of the CMV-IE promoter and SV40 late promoter sequences. To produce plasmid pCMV.BEV.SV40L.BEV, the translatable BEV polymerase structural gene present in pCR.BEV.2 (FIG. 7) was sub-cloned in the sense orientation as a BglII-to-BamHI fragment behind the SV40 late promoter sequence present in BamHI-digested pCMV.BEV.SV40L-O (FIG. 16).

Plasmid pCMV.BEV.SV40L.VEB

Plasmid pCMV.BEV.SV40L.VEB (FIG. 20) comprises a multiple structural gene unit comprising two BEV polymerase, structural genes placed operably and separately under control of the CMV-IE promoter and SV40 late promoter sequences. To produce plasmid pCMV.BEV.SV40L.VEB, the translatable BEV polymerase structural gene present in pCR.BEV.2 (FIG. 7) was sub-cloned in the antisense orientation as a BglII-to-BamHI fragment behind the SV40 late promoter sequence present in BamHI-digested pCMV.BEV.SV40L-O (FIG. 16). In this plasmid, the BEV polymerase structural gene is expressed in the sense orientation under control of the CMV-IE promoter to produce a translatable mRNA, whilst the BEV polymerase structural gene is also expressed under control of the SV40 promoter to produce an antisense mRNA species.

Plasmid pCMV.SV40LR.cass plasmid pCMV.SV40LR.cass (FIG. 21) comprises the SV40 late promoter sequence derived from plasmid pCR.SV40L (FIG. 4), sub-cloned as a SalI fragment into the SalI site of the plasmid pCMV.cass (FIG. 2), such that the CMV-IE or the SV40 late promoter may drive transcription of a structural gene or a multiple structural gene unit, in the sense or antisense orientation, as desired. A multiple cloning site is positioned between the opposing CMV-IE and SV40 late promoter sequences in this plasmid to facilitate the introduction of a structural gene sequence. In order for expression of a structural gene sequence to occur from this plasmid, it must be introduced with its own transcription termination sequence located at the 3' end, because there are no transcription termination sequences located between the opposing CMV-IE and SV40 late promoter sequences in this plasmid. Preferably, the structural gene sequence or multiple structural gene unit which is to be introduced into pCMV.SV40LR.cass will comprise both a 5' and a 3' polyadenylation signal as follows:

(i) where the structural gene sequence or multiple structural gene unit is to be expressed in the sense orientation from the CMV IE promoter sequence and/or in the antisense orientation from the SV40 late promoter, the 5' polyadenylation signal will be in the antisense orientation and the 3' polyadenylation signal will be in the sense orientation; and (ii) where the structural gene sequence or multiple structural gene unit is to be expressed in the antisense orientation from the CMV IE promoter sequence and/or in the sense orientation from the SV40 late promoter, the 5' polyadenylation signal will be in the sense orientation and the 3' polyadenylation signal will be in the antisense orientation.

Alternatively or in addition, suitably-oriented terminator sequences may be placed at the 5'-end of the CMV and SV40L promoters, as shown in FIG. 21.

Alternatively, plasmid pCMV.SV40LR.cass is further modified to produce a derivative plasmid which comprises two polyadenylation signals located between the CMV IE and SV40 lace promoter sequences, in appropriate orientations to facilitate expression of any structural gene located therebetween in the sense or antisense orientation from either the CMV IE promoter or the SV40 promoter sequence. The present invention clearly encompasses such derivatives.

Plasmid pCMV.BBV.SV40LR

Plasmid pCMV.BEV.SV40LR (FIG. 22) comprises a structural gene comprising the entire BEV polymerase open reading frame placed operably and separately under control of opposing CMV-IE promoter and SV40 late promoter sequences, thereby potentially producing BEV polymerase transcripts at least from both strands of the full-length BEV polymerase structural gene. To produce plasmid pCMV.BEV.SV40LR, the translatable BEV polymerase structural gene present in pCR.BEV.2 (FIG. 7) was sub-cloned, as a BglII-to-BamHI fragment, into the unique BglII site of plasmid pCMV.SV40LR.cass (FIG. 21), such that the BEV open reading frame is present in the sense orientation relative to the CMV-IE promoter sequence.

Those skilled in the art will recognise that it is possible to generate a plasmid wherein the BEV polymerase fragment from pCR.BEV.2 is inserted in the antisense orientation, relative to the CMV IE promoter sequence, using this cloning strategy. The present invention further encompasses such a genetic construct.

EXAMPLE 5

Synthetic Genes and Genetic Constructs Comprising the Tyrosinase Open Reading Frame Isolation of the Tyrosinase Open Reading Frame The tyrosinase structural gene is isolated by polymerase chain reaction, from mRNA derived from murine cells, using the following oligonucleotide primers under standard polymerase chain reaction conditions:

```
Tyr 5' (forward primer; SEQ ID NO: 9):
5'-CCCGGGGCTTAGTGTAAAACAGGCTGAGAG-3';
and Tyr 3' (reverse primer; SEQ ID NO: 10):
5'-CCCGGGCAAATCCCAGTCATTTCTTAGAAAC-3'.
```

Nucleotide residues 1 to 6 in each primer represent a SmaI cloning site. Nucleotides 7 to 30 of primer Tyr 5' correspond to the 5'-end of the murine tyrosinase cDNA sequence disclosed in GenBank Accession No. M20234 (Kwon et al. 1988). Nucleotides 7 to 31 of primer Tyr 3' correspond to the complement of the nucleotide sequence of the 3' end of the murine tyrosinase cDNA sequence.

Plasmid pCR.tyr

Plasmid pCR.tyr is produced by sub-cloning the amplified tyrosinase structural gene into plasmid pCR2.1 (Example 1), substantially according to the manufacturer's protocol. Plasmid pCR.tyr can be used as a base plasmid to produce a range of genetic constructs designed to express the tyrosinase structural gene or a multiple structural gene unit comprising same, under the control of one or more promoter sequences.

Plasmid pCMV.TYR

Figure 23:
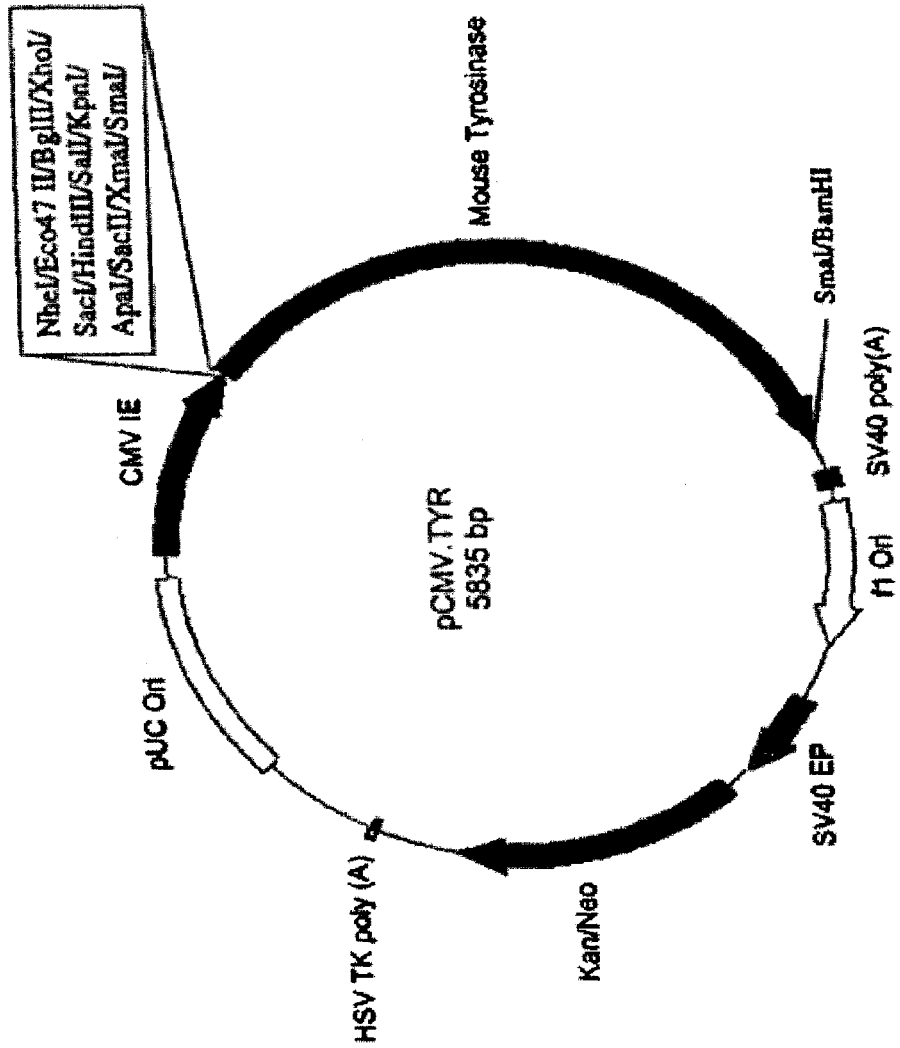
FIG. 23 is a copy of a diagrammatic representation of the plasmid pCMV.TYR.

Plasmid pCMV.TYR (FIG. 23) comprises the complete mouse tyrosinase cDNA sequence placed operably in connection, in the sense orientation, with the CMV-IE promoter sequence and upstream of the SV40 polyadenylation sequence. To produce pCMV.TYR, the full-length mouse tyrosinase cDNA sequence was excised from plasmid pCB-.tyr by digestion with SmaI and then ligated, into the SmaI cloning site of pCMV.cass (FIG. 2). Clones possessing the tyrosinase structural gene in the sense orientation relative to the CMV-IE promoter were then selected.

Plasmid pCMV.TYRLIB

Figure 24:
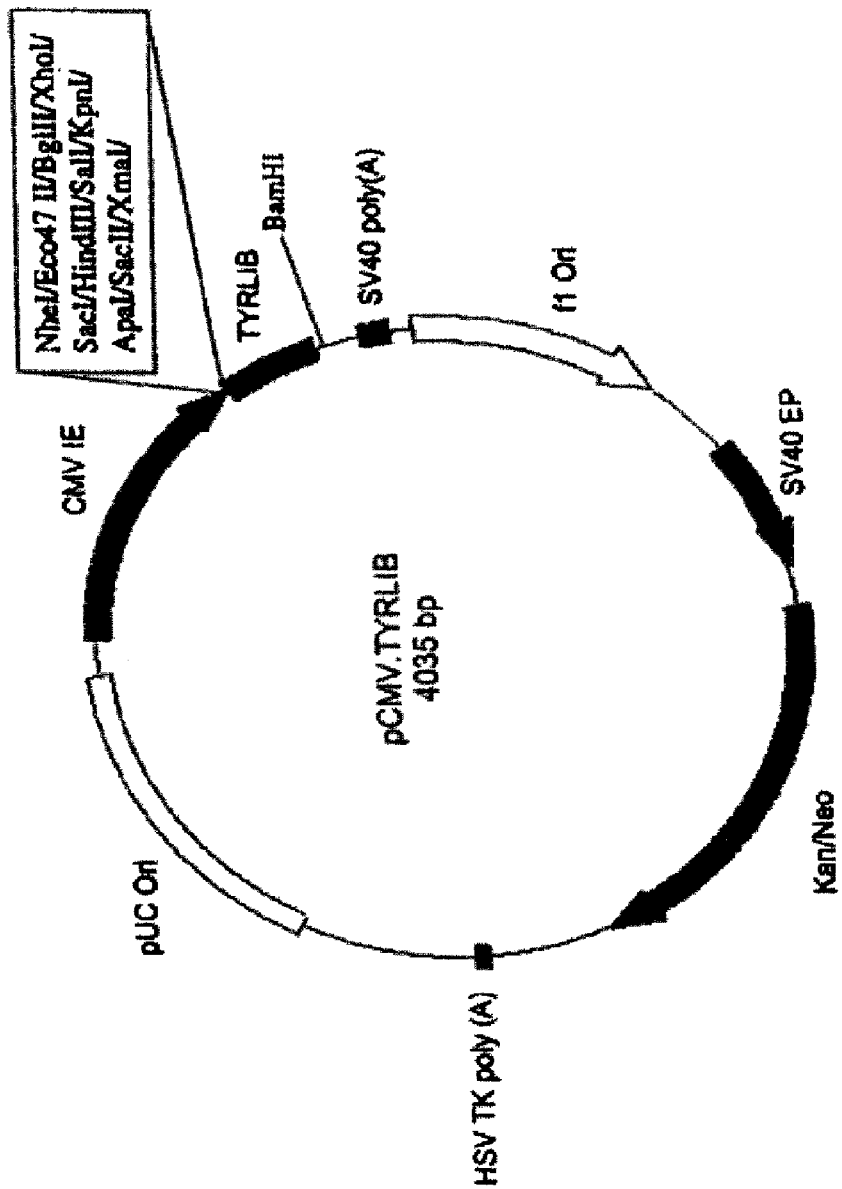
FIG. 24 is a copy of a diagrammatic representation of the plasmid pCMV.TYRLIB.

Plasmid pCMV.TYRLIB (FIG. 24) comprises a structural gene or multiple structural gene unit which comprises one or more tyrosinase gene fragments of 100 to 200 base pairs in length each, placed operably in connection with the CMV-IE promoter sequence and upstream of the SV40 polyadenylation signal. To produce pCMV.TYRLIB, blunt-ended fragments of the tyrosinase gene are ligated into SmaI-digested, dephosphorylated plasmid pCMV.cass DMA (FIG. 2). The tyrosinase gene fragments are produced, for example, by sonication or mechanical shearing and end-repair using T4 DNA polymerase. Accordingly, the structural gene insert in plasmid pCMV.TYRLIB is variable and an representative library of pCMV.TYRLIB plasmids, covering the complete tyrosinase gene sequence, may be produced using such procedures. The present invention clearly encompasses such representative libraries. Those skilled in the art will recognise that such procedures are also useful for structural genes other titan tyrosinase and, as a consequence, the present invention clearly extends to synthetic genes and genetic constructs wherein the structural gene present in pCMV.TYRLIB is a structural gene other than a tyrosinase gene fragment.

EXAMPLE 6

Synthetic Genes and Genetic Constructs
Comprising the lacI Open Reading Frame

Plasmid pCMV.Lac

Figure 25:
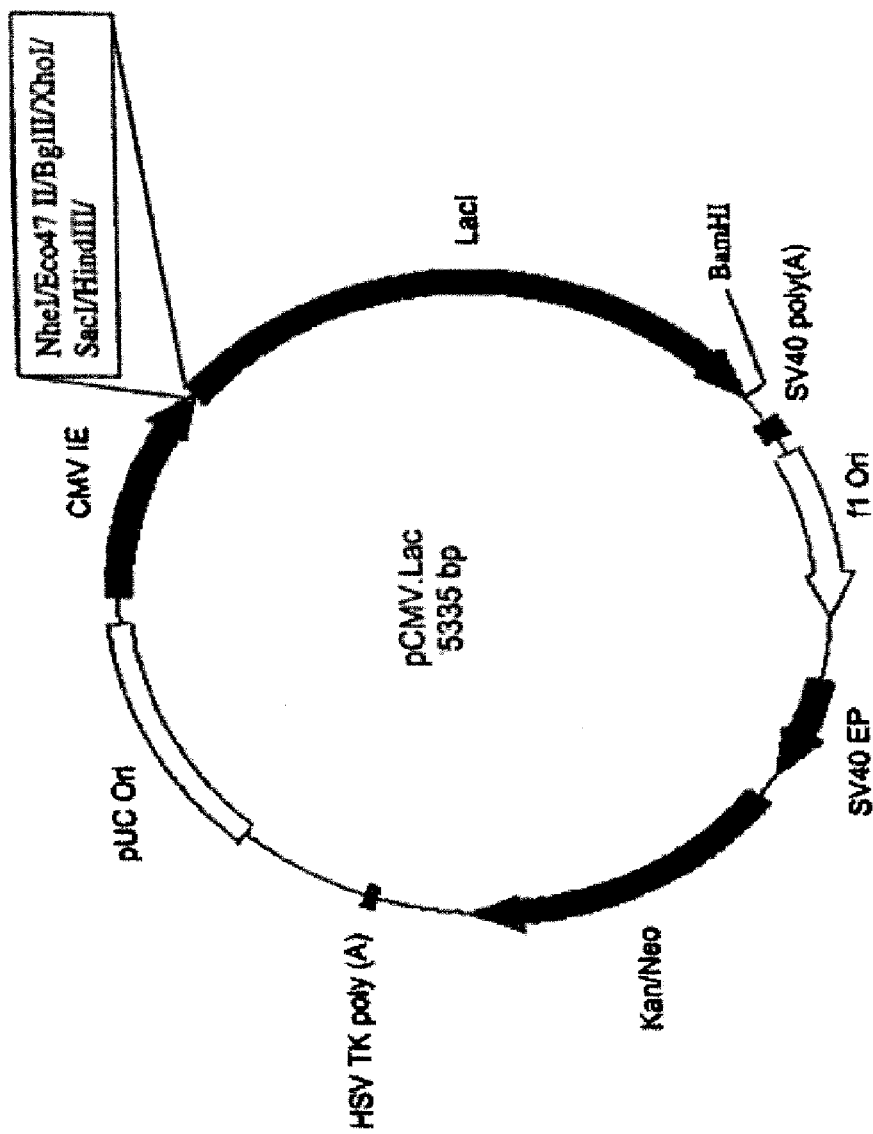
FIG. 25 is a copy of a diagrammatic representation of the plasmid pCMV.Lac.

Plasmid pCMV.Lac (FIG. 25) contains a CMV IE promoter driving expression of the lac repressor protein encoded by the *Escherichia coli* lacI gene. Accordingly, the open reading frame of the LacI gene is cloned in the sense orientation with respect to the CMV IE promoter sequence in this plasmid. This construct also contains the selectable marker for neomycin resistance.

To produce plasmid pCMV.Lac, the lacI gene was excised from plasmid pCMV.LacI (Stratagene) by digestion with HindIII and BsaBI and then ligated, in the sense orientation, into the multiple cloning site (MCS) of plasmid pCMV.cass (FIG. 2) which had been digested with HindIII and SmaI.

Plasmid pCMVLacI.OPRSV1.cass

Plasmid pCMVLacI-OPRSV1.cass (FIG. 26) is a dual expression construct in which the CMV-IE promoter drives expression of the LacI structural gene to produce the lac repressor protein and the OPRSVI promoter drives the expression of a second structural gene or multiple structural gene unit placed operably under control of lac repressor protein.

To produce plasmid pCMVLac.OPRSV1.cass, a DNA fragment comprising the OPRSV1 promoter, SV40 intron, lac operator sequence, multiple cloning site (MCS) and TK poly(A) sequence was excised from plasmid pOPRSVI/MCS (Stratagene), by digestion with SnaB1 and restriction enzymes, then end-filled using PfuI polymerase and ligated into the end-filled BglII cloning site of plasmid pCMVLacI (Stratagene).

EXAMPLE 7

Synthetic Genes and Genetic Constructs
Comprising the lacI and Green Fluorescent Protein
(GFP) open Reading Frames Plasmid pCMVLacI.OPRSV1.GFP.cass Plasmid pCMVLacI.OPRSV1.GFP.cass (FIG. 27) is designed such that a structural gene or multiple structural gene unit can be fused to the 3' untranslated region of the lacI gene, by cloning directly into the unique BsaB1 cloning site which is located after the lacI stop codon end before an SV40 polyadenylation signal. Alternatively, the BSAB1 site may be modified to facilitate cloning, for example by the addition of linkers or adaptors. This construct also contains the antibiotic selectable marker for hygromycin resistance.

Figure 26:
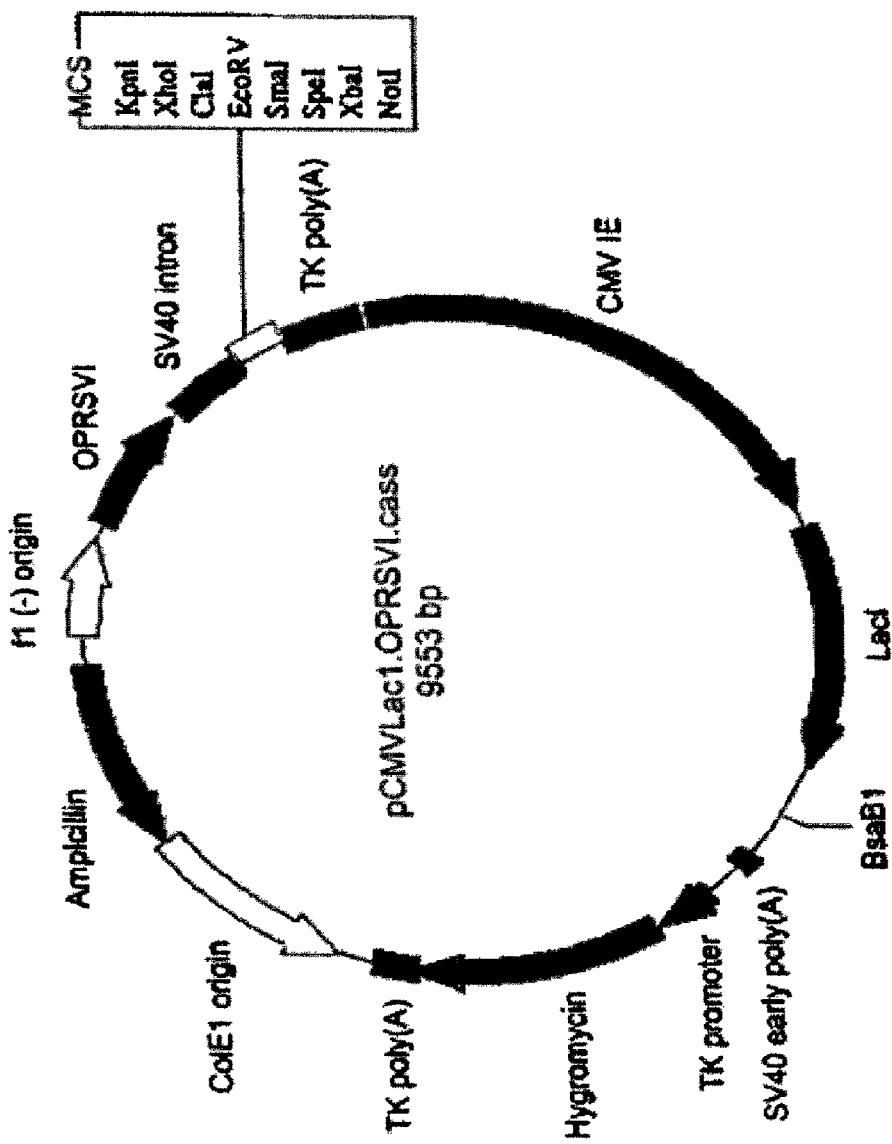
FIG. 26 is a copy of a diagrammatic representation of the plasmid pCMVLacI.OPRSV1.cass.

To produce plasmid pCMVLacI.OPRSVI.GFP.cass, the enhanced GFP coding sequence was excised from plasmid pEGFP-N1 MCS (FIG. 1) by digestion with XhoI and NotI and the DMA fragment thus produced was ligated into the XhoI and NotI cloning sites of the multiple cloning site present in plasmid pCMVLacI.OPRSVI.cass (FIG. 26).

EXAMPLE 8

Figure 28:
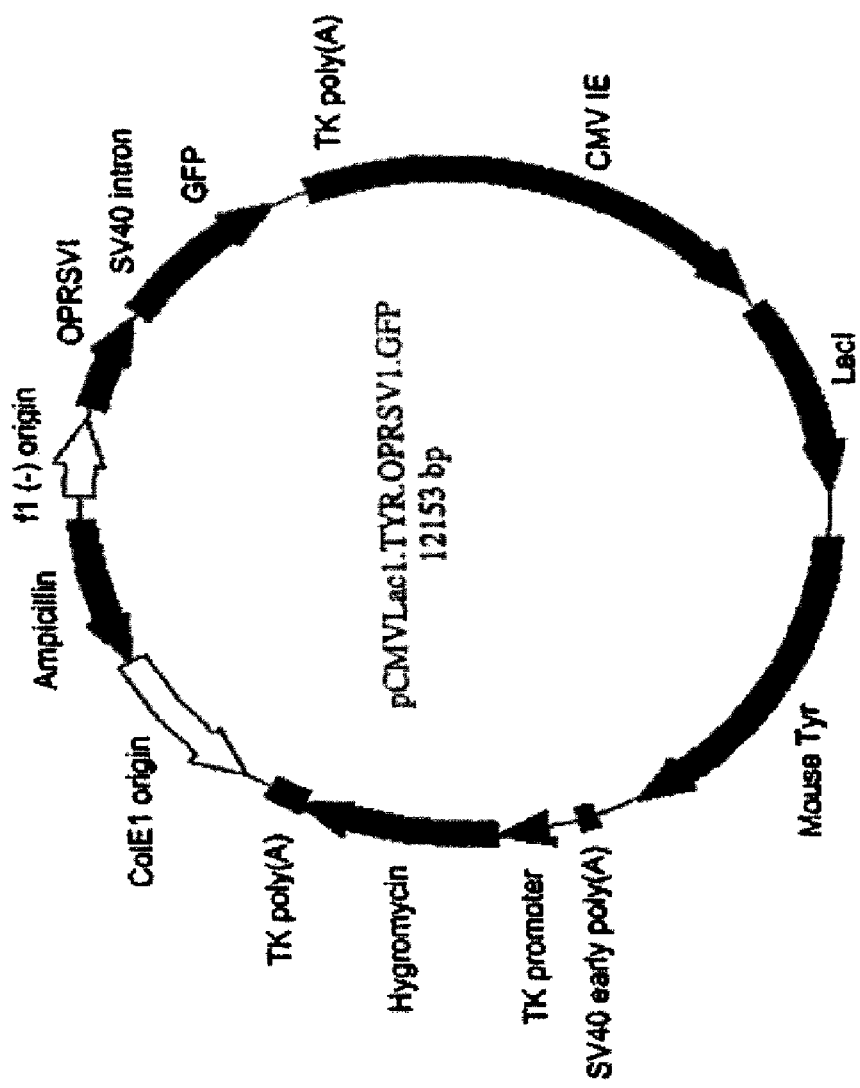
FIG. 28 is a copy of a diagrammatic representation of the plasmid pCMVLacI.TYR.OPRSV1.GFP.

Synthetic Genes and Genetic Constructs
Comprising the lacI and Green Fluorescent Protein
(GFP) and Tyrosinase Open Reading Frames Plasmid pCMVLacI.TYR.OPRSV1.GFP Plasmid pCMVLacI.TYR.OPRSV1.GFP (FIG. 28) is a dual construct in which the CMV IE promoter drives expression of the lacI gene and the mRNA of the mouse tyrosinase cDNA or a fragment thereof, whilst the OPRSV1 promoter drives expression of GFP operably under control of the lacI gene. The construct is designed such that the mouse tyrosinase gene is fused to the 3' untranslated region of the lacI gene via a unique BsaB1 cloning site. This cloning site is located after the stop codon of the lacI coding sequence, but before the SV40 polyadenylation signal. The construct also contains the hygromycin-resistance gene as a selection marker.

Figure 27:
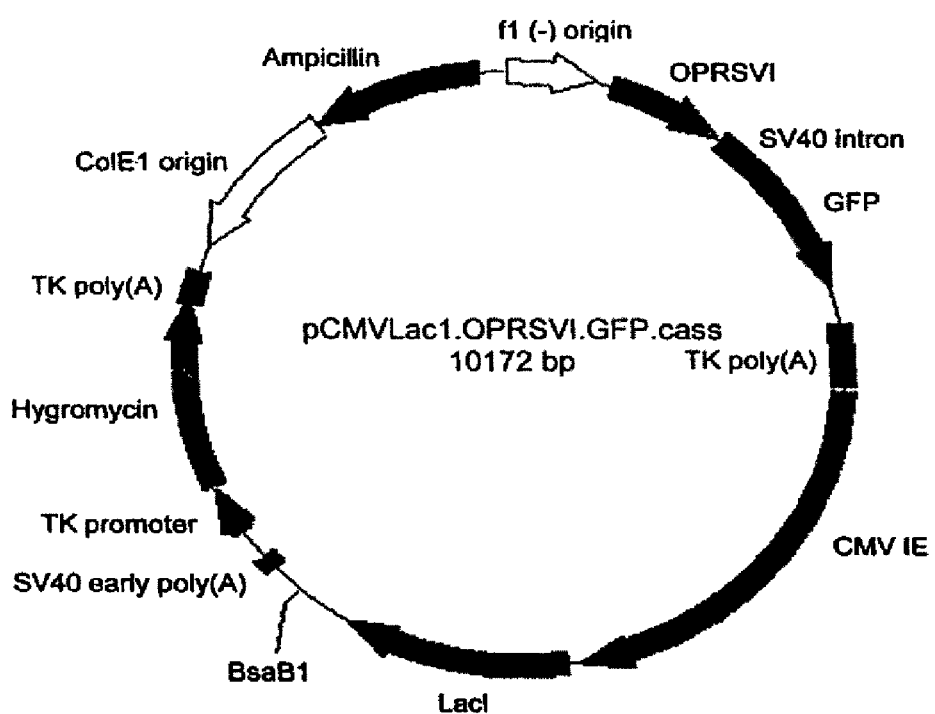
FIG. 27 is a copy of a diagrammatic representation of the plasmid pCMVLacI.OPRSV1.GFP.cass.

To produce plasmid pCMVLacI.TYR.OPRSV1.GFP, the complete tyrosinase gene present in plasmid pCR.tyr (Stratagene; Example 1) is isolated from host cells, digested with SmaI and ligated into BsaB1-digested and dephosphorylated plasmid pCMVLacI.OPRSVI.GFP.cass DNA (FIG. 27).

```
                           SEQUENCE LISTING (1) GENERAL INFORMATION:

(i) APPLICANT: Michael Wayne Graham, st al.

ii) TITLE OF INVENTION: Synthetic genes and genotic
        constructs comprising same I iii) NUMBER OF SEQUENCES: 10

(iv) CORRESPONDING ADDRESS:
        (A) ADDRESSEE: Scully, Scott, Murphy & Presser
        (B) STREET: 400 Garden City Plaza
        (C) CITY:. Garden City
        (D) STATE: New York
        (E) COUNTRY: USA
        (F) ZIP: 11530

(v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25

(vi) CURRENT APPLICATION DATA:
        (A) APPLICATION NUMBER:
        (B) FILING DATE: June 19, 1998

(viii) ATTORNEY/AGENT INFORMATION:
        (A) NAME: Frank S. DiGiglio (ix) TELECOMMUNICATION INFORMATION:
        (A) TELEPHONE: (516) 742-4343
        (B) TELEFAX: (516) 742-4366
        (C) TELEX:

(2) INFORMATION FOR SEQ ID NO: 1:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 1:
        CGGCAGATCT AACAATGGCA GGACAAATCG AGTACATC                    38

(2) INFORMATION FOR SEQ ID NO: 2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:
        CCCGGGATCC TCGAAAGAAT CGTACCACTT C                           31

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear
```

SEQUENCE LISTING (ii) MOLECULE TYPE: DNA (xi) SEQUENCE DESCRIPTION: SEQ ID NO: 3:
         GGGCGGATCC TTAGAAAGAA TCGTACCAC                                    29

(2) INFORMATION FOR SEQ ID NO: 4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:
         CGGCAGATCT GGACAAATCG AGTACATC                                     28

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:
         AGATCTGTAA ACGGCCACAA GTTCAG                                       26

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:
         GGATCCTTGT ACAGCTCGTC CATGCC                                       26

(2) INFORMATION FOR SEQ ID NO: 7:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:
         GTCGACAATA AAATATCTTT ATTTTCATTA CATCTGTGTG TTGGTTTTTT GTGTGATTTT  60

TGCAAAAGCC TAGG                                                    74

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:
         GTCGACGTTT AGAGCAGAAG TAACACTTCC G                                 31

```
SEQUENCE LISTING
```

(2) INFORMATION FOR SEQ ID NO: 9:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 9:
        CCCGGGGCTT AGTGTAAAAC AGGCTGAGAG                               30

(2) INFORMATION FOR SEQ ID NO: 10:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 10:
        CCCGGGCAAA TCCCAGTCAT TTCTTAGAAA C                             31

EQUIVALENTS

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two of mote of said steps or features.

REFERENCES

1. Ausubel, F. M. et al. (1987) In: Current Protocols in Molecular Biology, Wiley Interscience (ISBN 047140338).
2. Chalfie, M. et al (1994) *Science* 263: 302-805.
3. Cormack, B. et al (1996) *Gene* 173: 33-38.
4. Inouye, S, and Tsuji, F. I. (1994) *FEBS Letts.* 341: 277-280.
5. Kwon, B. S. et al. (1988) *Biochem. Biophys. Res. Comm.* 153:1301-1309.
6. Prasher, D. C. et al. (1992) *Gene* 111: 229-233.

```
                        SEQUENCE LISTING

<160> NUMBER OF SEQ ID NOS: 10

<210> SEQ ID NO 1
<211> LENGTH: 38
<212> TYPE: DNA
<213> ORGANISM: Artificial Sequence
<220> FEATURE:
<223> OTHER INFORMATION: Primer Bev-1

<400> SEQUENCE: 1
cggcagatct aacaatggca ggacaaatcg agtacatc                             38

<210> SEQ ID NO 2
<211> LENGTH: 31
<212> TYPE: DNA
<213> ORGANISM: Artificial Sequence
<220> FEATURE:
<223> OTHER INFORMATION: Primer Bev-2

<400> SEQUENCE: 2
cccgggatcc tcgaaagaat cgtaccactt c                                    31

<210> SEQ ID NO 3
```

```
<211> LENGTH: 29
<212> TYPE: DNA
<213> ORGANISM: Artificial Sequence
<220> FEATURE:
<223> OTHER INFORMATION: Primer Bev-3

<400> SEQUENCE: 3
gggcggatcc ttagaaagaa tcgtaccac                                    29

<210> SEQ ID NO 4
<211> LENGTH: 28
<212> TYPE: DNA
<213> ORGANISM: Artificial Sequence
<220> FEATURE:
<223> OTHER INFORMATION: Primer Bev-4

<400> SEQUENCE: 4
cggcagatct ggacaaatcg agtacatc                                     28

<210> SEQ ID NO 5
<211> LENGTH: 26
<212> TYPE: DNA
<213> ORGANISM: Artificial Sequence
<220> FEATURE:
<223> OTHER INFORMATION: Primer Bgl-GFP

<400> SEQUENCE: 5
agatctgtaa acggccacaa gttcag                                       26

<210> SEQ ID NO 6
<211> LENGTH: 26
<212> TYPE: DNA
<213> ORGANISM: Artificial Sequence
<220> FEATURE:
<223> OTHER INFORMATION: Primer GFP-Bam

<400> SEQUENCE: 6
ggatccttgt acagctcgtc catgcc                                       26

<210> SEQ ID NO 7
<211> LENGTH: 74
<212> TYPE: DNA
<213> ORGANISM: Artificial Sequence
<220> FEATURE:
<223> OTHER INFORMATION: Primer SV40-1

<400> SEQUENCE: 7
gtcgacaata aaatatcttt attttcatta catctgtgtg ttggttttttt gtgtgatttt    60 tgcaaaagcc tagg                                                    74

<210> SEQ ID NO 8
<211> LENGTH: 31
<212> TYPE: DNA
<213> ORGANISM: Artificial Sequence
<220> FEATURE:
<223> OTHER INFORMATION: Primer SV40-2

<400> SEQUENCE: 8
gtcgacgttt agagcagaag taacacttcc g                                 31

<210> SEQ ID NO 9
<211> LENGTH: 30
<212> TYPE: DNA
<213> ORGANISM: Artificial Sequence
<220> FEATURE:
<223> OTHER INFORMATION: Forward Primer Tyr 5'
```

```
<400> SEQUENCE: 9 cccgggctt agtgtaaaac aggctgagag                                    30

<210> SEQ ID NO 10
<211> LENGTH: 31
<212> TYPE: DNA
<213> ORGANISM: Artificial Sequence
<220> FEATURE:
<223> OTHER INFORMATION: Reverse Primer Tyr 3'

<400> SEQUENCE: 10
cccgggcaaa tcccagtcat ttcttagaaa c                                 31
```

The invention claimed is:

1. A double-stranded DNA construct comprising a first structural gene sequence comprising 20 consecutive nucleotides identical in sequence to a region of a target gene in an animal cell; a second structural gene sequence comprising 20 consecutive nucleotides identical in sequence to, and in an inverted orientation relative to, the 20 consecutive nucleotides of the first structural gene sequence, such that a repeating sequence which comprises the 20 consecutive nucleotides in length identical to the region of the target gene is present in the DNA construct; a stuffer fragment which consists of nucleotides other than the nucleotides of the repeating sequence and which separates and links the first and second structural gene sequences; a promoter and a transcription termination sequence, wherein the repeating sequence within the DNA construct comprises 20 nucleotides in length, and wherein the first structural gene sequence, the stuffer fragment and the second structural gene sequence are all operably connected to the promoter and the transcription termination sequence.

2. The double-stranded DNA construct of claim 1, wherein the target gene is endogenous to the animal cell.

3. The double-stranded DNA construct of claim 1, wherein the target gene is non-endogenous to the animal cell.

4. The double-stranded DNA construct of claim 1, wherein the region of the target gene is in an exon.

5. The double-stranded DNA construct of claim 1, wherein the target gene is from a lentivirus.

6. The double-stranded DNA construct of claim 1, wherein the target gene is from a single-stranded (+) RNA virus.

7. The double-stranded DNA construct of claim 1, wherein the animal cell is an insect cell.

8. An isolated animal cell, tissue or organ, having a DNA comprising a first structural gene sequence comprising 20 consecutive nucleotides identical in sequence to a region of a target gene in the animal cell; a second structural gene sequence comprising 20 consecutive nucleotides identical in sequence to, and in an inverted orientation relative to, the 20 consecutive nucleotides of the first structural gene sequence, such that a repeating sequence which comprises the 20 consecutive nucleotides in length identical to the region of the target gene is present in the DNA, a stuffer fragment which consists of nucleotides other than the nucleotides of the repeating sequence and which is between and links the first and second structural gene sequences; a promoter and a transcription termination sequence, wherein the repeating sequence within the DNA comprises 20 nucleotides in length, and wherein the first structural gene sequence, the stuffer fragment and the second structural gene sequence are all operably connected to the promoter and the transcription termination sequence.

9. The isolated animal cell of claim 8, wherein the target gene is endogenous to the animal cell.

10. The isolated animal cell of claim 8, wherein the target gene is non-endogenous to the animal cell.

11. The isolated animal cell, tissue or organ of claim 8, wherein the region of the target gene is in an exon.

12. The isolated animal cell, tissue or organ of claim 8, wherein the target gene is from a lentivirus.

13. The isolated animal cell, tissue or organ of claim 8, wherein the target gene is from a single-stranded (+) RNA virus.

14. The isolated animal cell, tissue or organ of claim 8, wherein the DNA is integrated into the genome of the isolated animal cell, tissue or organ.

15. The isolated animal cell of claim 8, wherein the animal cell is an insect cell.

* * * * *